(12) United States Patent
Kurt-Jones et al.

(10) Patent No.: US 8,748,403 B2
(45) Date of Patent: Jun. 10, 2014

(54) MODULATION OF HSV INFECTION

(75) Inventors: Evelyn A. Kurt-Jones, Belmont, MA (US); Robert W. Finberg, Sudbury, MA (US)

(73) Assignee: University of Massachusetts, Boston, MA (US)

( * ) Notice: Subject to any disclaimer, the term of this patent is extended or adjusted under 35 U.S.C. 154(b) by 1311 days.

(21) Appl. No.: 11/041,065

(22) Filed: Jan. 21, 2005

(65) Prior Publication Data

US 2005/0164172 A1    Jul. 28, 2005

Related U.S. Application Data

(60) Provisional application No. 60/538,324, filed on Jan. 22, 2004.

(51) Int. Cl.
| | |
|---|---|
| *C12N 15/11* | (2006.01) |
| *C07H 21/02* | (2006.01) |
| *C07H 21/04* | (2006.01) |
| *A61K 48/00* | (2006.01) |

(52) U.S. Cl.
USPC ........................................ 514/44 A; 536/24.5

(58) Field of Classification Search
USPC ............... 514/44; 536/23.1, 24.3, 24.33, 24.5
See application file for complete search history.

(56) References Cited

FOREIGN PATENT DOCUMENTS

| | | |
|---|---|---|
| JP | 2006/503970 | 2/2006 |
| WO | WO 01/36488 | 5/2001 |
| WO | 2004/083455 | 9/2004 |

OTHER PUBLICATIONS

Braasch, D. A. Novel antisense and peptide nucleic acid strategies for controlling gene expression. Biochemistry. Apr. 2002; 41(14): 4503-4510.*
Branch, A. D. A good antisense molecule is hard to find. Trends Biochem Sci. Feb. 1998;23(2):45-50.*
Gewirtz et al. Facilitating oligonucleotide delivery: Helping antisense deliver on its promise. Proc. Natl. Acad. Sci. 1996. v 93, pp. 3161-3163.*
Tamm, I. et al. Antisense therapy in oncology: new hope for an old idea. The Lancet. Aug. 2001 358: 489-497.*
Agrawal et al. Antisense therapeutics: is it as simple as complementary base recognition? Molecular Medicine Today, vol. 6, p. 72-81, Feb. 2000.*
Lu et al. (2005). Deliverying siRNA in vivo for functional genomics and novel therapeutics. From RNA Interference Technology (Cambridge, Appasani, ed., pp. 303-317).*
Downward, J. Science, medicine, and the future. RNA interference. BMJ, 2004 vol. 328:1245-1248.*
Nielsen, PE. Systemic delivery. The last hurdle? Gene Therapy, 2005 vol. 12:956-957.*
Homo sapiens toll-like receptor 2 (TLR2) mRNA, NCBI sequence for NM_003264.2. Downloaded on Sep. 6, 2011 from http://www.ncbi.nlm.nih.gov/nuccore/NM_003264.2.*
Homo sapiens toll-like receptor 2 (TLR2) mRNA, NCBI sequence for NM_003264.2. Downloaded on Sep. 8, 2011 from http://www.ncbi.nlm.nih.gov/nuccore/NM_003264.3.*
Koedel et al., "Toll-like receptor 2 participates in mediation of immune response in experimental pneumococcal meningitis," J. Immunol. 170(1):438-44 (2003).

(Continued)

*Primary Examiner* — Terra Cotta Gibbs
(74) *Attorney, Agent, or Firm* — Fish & Richardson P.C.

(57) ABSTRACT

Toll-like receptor 2 (TLR2) has been found to mediate certain effects of HSV infection, particularly in neonates. Compounds that decrease TLR2 expression or activity are useful for ameliorating such deleterious effects.

16 Claims, 6 Drawing Sheets

(56) References Cited

OTHER PUBLICATIONS

Kurt-Jones et al., "Pattern recognition receptors TLR4 and CD14 mediate response to respiratory syncytial virus," Nat. Immunol. 1(5):398-401 (2000).

Reiling et al., "Cutting edge: Toll-like receptor (Tlr)2- and TLR4-mediated pathogen recognition in resistance to airborne infection with Mycobacterium tuberculosis," J. Immunol. 169(7):3480-4 (2002).

Haynes et al., "Involvement of toll-like receptor 4 in innate immunity to respiratory syncytial virus," J. Virol. 75(22):10730-737 (2001).

Compton et al., "Human cytomegalovirus activates inflammatory cytokine responses via CD14 and Toll-like receptor 2," J. Virol. 77(8):4588-96 (2003).

International Search Report mailed Jun. 14, 2005 from PCT/US05/02128.

Boivin et al., "Intranasal herpes simplex virus 2 inoculation causes a profound thymidine kinase dependant cerebral inflammatory response in the mouse hindbrain," *European Journal of Neuroscience*, 16(1):29-43 (2002).

Kurt-Jones et al., "Herpes simplex virus 1 interaction with Toll-like receptor 2 contributes to lethal encephalitis," *PNAS*, 101(5):1315-1320 (2004).

Elbashir et al., "Analysis of gene function in somatic mammalian cells using small interfering RNAs," Methods, 26:199-213, 2002.

Goyenvalle et al., "Rescue of Dystrophic Muscle Through U7 snRNA—Mediated Exon Skipping," Science, 306:1796-1799, 2004.

Soutschek et al., "Therapeutic silencing of an endogenous gene by systemic administration of modified siRNAs," Nature, 432:173-178, 2004.

Wang et al., "Varicella-Zoster Virus Activates Inflammatory Cytokines in Human Monocytes and Macrophages via Toll-Like Receptor 2," J. Virol., 79:12658-12666, 2005.

European Office Action; Application No. 05711884.6-1223; mailed Nov. 2, 2009, Applicant: University of Massachusetts; entitled Modulation of HSV Infection; pp. 1-5.

European Office Action; Application No. 05711884.6-1223; mailed Mar. 25, 2008, Applicant: University of Massachusetts; entitled Modulation of HSV Infection; pp. 1-6.

European Office Action; Application No. 05711884.6-1223; mailed Jul. 23, 2008; Applicant: University of Massachusetts; entitled Modulation of HSV Infection; pp. 1-4.

Canadian Office Action; Application No. 2,554,203, mailed Dec. 7, 2011, Applicant: University of Massachusetts; entitled: Modulation of HSV Infection; pp. 1-2.

European Office Action; Application no. 05711884.6—1223; mailed Nov. 2, 2009, Applicant: University of Massachusetts; entitled Modulation of HSV Infection; pp. 1-5.

European Office Action; Application no. 05711884.6—1223; mailed Mar. 25, 2008, Applicant: University of Massachusetts; entitled Modulation of HSV Infection; pp. 1-6.

European Office Action; Application No: 05711884.6—1223; mailed Jul. 23, 2008; Applicant: University of Massachusetts; entitled Modulation of HSV Infection; pp. 1-4.

Japanese Office Action; Application No. 2006-551353; mailed Nov. 8, 2012; Applicant: University of Massachusetts; entitled Modulation of HSV Infection; pp. 1-8.

\* cited by examiner

SEQUENCE LISTING

```
<160> NUMBER OF SEQ ID NOS: 2

<210> SEQ ID NO 1
<211> LENGTH: 2621
<212> TYPE: DNA
<213> ORGANISM: Homo sapiens

<400> SEQUENCE: 1
cagtgtttgg tgttgcaagc aggatccaaa ggagacctat agtgactccc aggagctctt      60
agtgaccaag tgaaggtacc tgtggggctc attgtgccca ttgctctttc actgctttca     120
actggtagtt gtgggttgaa gcactggaca atgccacata ctttgtggat ggtgtgggtc     180
ttgggggtca tcatcagcct ctccaaggaa gaatcctcca atcaggcttc tctgtcttgt     240
gaccgcaatg gtatctgcaa gggcagctca ggatctttaa actccattcc ctcagggctc     300
```

| | |
|---|---|
| acagaagctg taaaaagcct tgacctgtcc aacaacagga tcacctacat tagcaacagt | 360 |
| gacctacaga ggtgtgtgaa cctccaggct ctggtgctga catccaatgg aattaacaca | 420 |
| atagaggaag attcttttc ttccctgggc agtcttgaac atttagactt atcctataat | 480 |
| tacttatcta atttatcgtc ttcctggttc aagccccttt cttctttaac attcttaaac | 540 |
| ttactgggaa atccttacaa aaccctaggg gaaacatctc ttttttctca tctcacaaaa | 600 |
| ttgcaaatcc tgagagtggg aaatatggac accttcacta agattcaaag aaaagatttt | 660 |
| gctggactta ccttccttga ggaacttgag attgatgctt cagatctaca gagctatgag | 720 |
| ccaaaaagtt tgaagtcaat tcagaatgta agtcatctga tccttcatat gaagcagcat | 780 |
| attttactgc tggagatttt tgtagatgtt acaagttccg tggaatgttt ggaactgcga | 840 |
| gatactgatt tggacacttt ccattttca gaactatcca ctggtgaaac aaattcattg | 900 |
| attaaaaagt ttacatttag aaatgtgaaa atcaccgatg aaagtttgtt tcaggttatg | 960 |
| aaacttttga atcagatttc tggattgtta gaattagagt ttgatgactg taccccttaat | 1020 |
| ggagttggta attttagagc atctgataat gacagagtta tagatccagg taaagtggaa | 1080 |
| acgttaacaa tccggaggct gcatattcca aggttttact tattttatga tctgagcact | 1140 |
| ttatattcac ttacagaaag agttaaaaga atcacagtag aaaacagtaa agttttctg | 1200 |
| gttccttgtt tactttcaca acatttaaaa tcattagaat acttggatct cagtgaaaat | 1260 |
| ttgatggttg aagaatactt gaaaaattca gcctgtgagg atgcctggcc ctctctacaa | 1320 |
| actttaattt taaggcaaaa tcatttggca tcattggaaa aaccggaga ctttgctc | 1380 |
| actctgaaaa acttgactaa cattgatatc agtaagaata gttttcattc tatgcctgaa | 1440 |
| acttgtcagt ggccagaaaa gatgaaatat ttgaacttat ccagcacacg aatacacagt | 1500 |
| gtaacaggct gcattcccaa gacactggaa attttagatg ttagcaacaa caatctcaat | 1560 |
| ttatttct tgaatttgcc gcaactcaaa gaactttata tttccagaaa taagttgatg | 1620 |
| actctaccag atgcctccct cttacccatg ttactagtat tgaaaatcag taggaatgca | 1680 |
| ataactacgt tttctaagga gcaacttgac tcatttcaca cactgaagac tttggaagct | 1740 |
| ggtggcaata acttcatttg ctcctgtgaa ttcctctcct tcactcagga gcagcaagca | 1800 |
| ctggccaaag tcttgattga ttggccagca aattacctgt gtgactctcc atcccatgtg | 1860 |
| cgtggccagc aggttcagga tgtccgcctc tcggtgtcgg aatgtcacag acagcactg | 1920 |
| gtgtctggca tgtgctgtgc tctgttcctg ctgatcctgc tcacgggggt cctgtgccac | 1980 |
| cgtttccatg gcctgtggta tatgaaaatg atgtgggcct ggctccaggc caaaaggaag | 2040 |
| cccaggaaag ctcccagcag gaacatctgc tatgatgcat ttgtttctta cagtgagcgg | 2100 |
| gatgcctact gggtggagaa ccttatggtc caggagctgg agaacttcaa tccccccttc | 2160 |
| aagttgtgtc ttcataagcg ggacttcatt cctggcaagt ggatcattga caatatcatt | 2220 |
| gactccattg aaaagagcca caaaactgtc tttgtgcttt ctgaaaactt tgtgaagagt | 2280 |
| gagtggtgca gtatgaact ggacttctcc catttccgtc tttttgatga gaacaatgat | 2340 |
| gctgccattc tcattcttct ggagcccatt gagaaaaaag ccattcccca gcgcttctgc | 2400 |
| aagctgcgga agataatgaa caccaagacc tacctggagt ggcccatgga cgaggctcag | 2460 |
| cgggaaggat tttgggtaaa tctgagagct gcgataaagt cctaggttcc catatttaag | 2520 |
| accagtcttt gtctagttgg gatctttatg tcactagtta tagttaagtt cattcagaca | 2580 |
| taattatata aaaactacgt ggatgtaccg tcatttgagg a | 2621 |

```
<210> SEQ ID NO 2
<211> LENGTH: 784
<212> TYPE: PRT
<213> ORGANISM: Homo sapiens

<400> SEQUENCE: 2

Met Pro His Thr Leu Trp Met Val Trp Val Leu Gly Val Ile Ile Ser
 1               5                  10                  15

Leu Ser Lys Glu Glu Ser Ser Asn Gln Ala Ser Leu Ser Cys Asp Arg
             20                  25                  30

Asn Gly Ile Cys Lys Gly Ser Ser Gly Ser Leu Asn Ser Ile Pro Ser
         35                  40                  45

Gly Leu Thr Glu Ala Val Lys Ser Leu Asp Leu Ser Asn Asn Arg Ile
     50                  55                  60

Thr Tyr Ile Ser Asn Ser Asp Leu Gln Arg Cys Val Asn Leu Gln Ala
 65                  70                  75                  80

Leu Val Leu Thr Ser Asn Gly Ile Asn Thr Ile Glu Glu Asp Ser Phe
                 85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
    370                 375                 380
```

```
Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
            405                 410                 415

Asn Ile Asp Ile Ser Lys Asn Ser Phe His Ser Met Pro Glu Thr Cys
        420                 425                 430

Gln Trp Pro Glu Lys Met Lys Tyr Leu Asn Leu Ser Ser Thr Arg Ile
    435                 440                 445

His Ser Val Thr Gly Cys Ile Pro Lys Thr Leu Glu Ile Leu Asp Val
450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
            485                 490                 495

Leu Leu Pro Met Leu Leu Val Leu Lys Ile Ser Arg Asn Ala Ile Thr
        500                 505                 510

Thr Phe Ser Lys Glu Gln Leu Asp Ser Phe His Thr Leu Lys Thr Leu
    515                 520                 525

Glu Ala Gly Gly Asn Asn Phe Ile Cys Ser Cys Glu Phe Leu Ser Phe
530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
            565                 570                 575

Asp Val Arg Leu Ser Val Ser Glu Cys His Arg Thr Ala Leu Val Ser
        580                 585                 590

Gly Met Cys Cys Ala Leu Phe Leu Leu Ile Leu Leu Thr Gly Val Leu
    595                 600                 605

Cys His Arg Phe His Gly Leu Trp Tyr Met Lys Met Met Trp Ala Trp
610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
            645                 650                 655

Asn Leu Met Val Gln Glu Leu Glu Asn Phe Asn Pro Pro Phe Lys Leu
        660                 665                 670

Cys Leu His Lys Arg Asp Phe Ile Pro Gly Lys Trp Ile Ile Asp Asn
    675                 680                 685

Ile Ile Asp Ser Ile Glu Lys Ser His Lys Thr Val Phe Val Leu Ser
690                 695                 700

Glu Asn Phe Val Lys Ser Glu Trp Cys Lys Tyr Glu Leu Asp Phe Ser
705                 710                 715                 720

His Phe Arg Leu Phe Asp Glu Asn Asn Asp Ala Ala Ile Leu Ile Leu
            725                 730                 735

Leu Glu Pro Ile Glu Lys Lys Ala Ile Pro Gln Arg Phe Cys Lys Leu
        740                 745                 750

Arg Lys Ile Met Asn Thr Lys Thr Tyr Leu Glu Trp Pro Met Asp Glu
    755                 760                 765

Ala Gln Arg Glu Gly Phe Trp Val Asn Leu Arg Ala Ala Ile Lys Ser
770                 775                 780
```

MODULATION OF HSV INFECTION

CLAIM OF PRIORITY

This application claims priority under 35 USC §119(e) to U.S. Patent Application Ser. No. 60/538,324, filed on Jan. 22, 2004, the entire contents of which are hereby incorporated by reference.

FEDERALLY SPONSORED RESEARCH OR DEVELOPMENT

This invention was made with Government support under Grants Nos. R01 AI49309, R01 AI51415, PO1 NS35138, RO1 GM63244, and RO1 AI39576 awarded by the National Institutes of Health. The Government has certain rights in the invention.

TECHNICAL FIELD

This invention relates to methods and compounds for treating viral infection.

BACKGROUND

Herpes simplex virus 1 (HSV-1) causes life-long infection and periodic disease in the majority of the world's human population (see, e.g., Corey, Herpes Simplex Viruses, in Braunwald et al., Eds., *Harrison's Principles of Internal Medicine*. 15th ed. New York: McGraw Hill, 2001, Chap. 182, pp. 1100-1106; and Whitley et al., N. Engl. J. Med., 324: 450-4 (1991)). Herpes group viruses (including HSV, VZV, and CMV), usually cause only limited disease in adults and older children.

In humans, HSV-1 is usually acquired in childhood, and often presents as a self-limiting pharyngitis. Reactivation of HSV-1 infection is associated with peri-oral lesions, sometimes termed "cold sores" or "fever blisters." Neonates (most often at less than one week of age) with HSV (either HSV-1 or HSV-2) infections, however, may present with a "sepsis-like" syndrome that, although rare, can be devastating, and is often characterized by blood pressure instability, shock, fever, jaundice, hepatosplenomegaly, and the development of disseminated intravascular coagulation, symptoms commonly seen in serious TORCH infections (Toxoplasmosis, Other infections, Rubella, Cytomegalovirus, and Herpes) (Id.), as well as lethal encephalitis (Whitely, 2001, in *Fields' Virology*, Knipe, ed., Chapter 73, Lippincott, Williams, & Wilkins, Philadelphia, Pa.; Whitley et al., N. Engl. J. Med. 324: 450-454 (1991)). Herpes simplex virus type 2 (HSV-2) is a major cause of neonatal encephalitis. The primary route of infection is via the maternal birth canal, although, infrequently, hematogenous transplacental in utero infection can occur. The CNS is involved in approximately 30% of infected infants. Infection can result in seizures, microcephaly, microphthalmia, ventriculomegaly, multicystic encephalomalacia and death. Pathological examination demonstrates acute and chronic parenchymal and leptomeningeal inflammation. In contrast to the temporal/frontal predilection seen in adults, HSV neonatal infection is diffuse and may therefore result in widespread brain destruction.

Herpes simplex 1 (HSV-1) is also the most common diagnosed cause of sporadic (non-epidemic) encephalitis in humans. Without early treatment, HSV-1 encephalitis is a devastating disease that is typically fatal. Among survivors, serious residual defects are commonly seen. While HSV causes a variety of illnesses in immunocompromised hosts, including disseminated infection, pneumonia, and hepatitis, encephalitis is also commonly seen in patients with normal immune responses.

SUMMARY

The invention is based, in part, on the finding that Toll-like receptor 2 (TLR2) mediates the inflammatory cytokine response to Herpes Simplex Virus (HSV)-1 and HSV-2, and that TLR2 expression is associated with lethal viral encephalitis resulting from HSV-1 infection. Further, the invention is based, in part, on the finding that the neonatal HSV-induced sepsis is related to TLR2 activation. Thus, the invention includes compounds for the treatment of disorders associated with HSV infection, methods for identifying such compounds, and methods for using such compounds.

Accordingly, the invention relates to methods of identifying candidate compounds for treating HSV (e.g., HSV-1 or HSV-2) infection. The methods include the steps of identifying a test compound that inhibits TLR2 expression or activity, administering the test compound to a cell infected with HSV, and determining whether the compound inhibits at least one indicator of HSV infection in the cell, such that a compound that inhibits HSV infection in the cell is a candidate compound for treating HSV infection.

Thus, the invention includes methods for identifying candidate therapeutic compounds for the treatment of herpes simplex virus (HSV) infection. The methods include obtaining a candidate compound that is known to inhibit TLR2 expression or activity; administering the candidate compound to a cell, e.g., a mammalian cell such as a human or murine cell, that is infected with HSV, e.g., HSV-1 or HSV-2; and determining whether the candidate compound inhibits at least one indicator of HSV infection in the cell, e.g., transcription factor activation (e.g., Nuclear Factor-kappa B (NF-κB)), chemokine secretion or cytokine secretion (e.g., one or more of IL-1, IL-6, IL-8, Tumor Necrosis Factor (TNF), Monocyte Chemoattractant Protein-I (MCP-1), or Macrophage Inflammatory Protein-I (MIP-1)). A test compound that inhibits an indicator of HSV infection in the cell is a candidate therapeutic compound for the treatment of HSV infection.

In some embodiments, the cell is in a living mammal, e.g., a mouse or a human, and the method is carried out by administering the candidate compound to the mammal.

In some embodiments, the symptom is a symptom of encephalopathy, e.g., one or more of malaise, fever, headache, nausea, lethargy, confusion, delirium, seizures, aphasia, cranial nerve deficits, and hemiparesis.

In some embodiments, the mammal is a neonate and the symptom is a symptom of TORCH syndrome, e.g., fever, difficulties feeding, hepatosplenomegaly, cutaneous manifestations (e.g., petechiae, purpura, jaundice, and dermal erythropoiesis), hearing impairment, and abnormalities of the eyes.

In some embodiments, the symptom is selected from the group consisting of blisters on the cornea, skin or mucous membranes, itching, burning, soreness, skin ulcers, enlarged and/or painful lymph nodes in the groin, blurred vision, headache, fever, burning during urination, and general malaise.

In some embodiments, the cell is in a test population of mammals (e.g., the method is carried out in a test population), and the indicator of HSV infection in the mammal is at least one symptom of encephalopathy or TORCH syndrome, wherein a decrease in the severity of the symptom in the population of mammals compared to a control population of mammals indicates that the compound is a candidate compound for treating HSV infection.

In some embodiments, the candidate compound is a TLR2 antisense oligonucleotide or small interfering RNA (siRNA), a TLR2 dominant negative polypeptide, a TLR2 extracellular binding domain, or an anti-TLR2 antibody or antigen-binding fragment thereof. In some embodiments, the candidate compound specifically binds to TLR2.

In some embodiments, obtaining a candidate compound that is known to inhibit TLR2 expression or activity includes obtaining a sample comprising TLR2; contacting the sample with a test compound; evaluating expression or activity of the TLR2 in the sample; and selecting a test compound that inhibits TLR2 expression or activity in the sample. The test compounds can be, e.g., nucleic acids, polypeptides, peptides, peptoids, antibodies, non-peptide oligomers, and small molecules.

In another aspect, the invention includes methods for treating herpes simplex virus (HSV, e.g., HSV-1 or HSV-2) infection in a subject, by identifying a subject in need of treatment for HSV infection, and administering to the subject a therapeutically effective amount of a candidate compound that decreases TLR2 expression or activity, thereby treating HSV infection in the subject.

In some embodiments, the subject is a mammal, e.g., a human, e.g., a neonate, a child, or an adult. In some embodiments, the subject has at least one symptom of encephalopathy.

In a further aspect, the invention features methods for inhibiting or treating a herpes simplex virus (HSV) infection in a cell, e.g., a cell in a mammal, e.g., a human. The methods include identifying a cell that is susceptible to HSV infection or a cell that is HSV infected, e.g., infected with HSV-1 or HSV-2; and contacting the cell with a candidate compound that can inhibit TLR-2 expression or activity in an amount and for a time sufficient to inhibit TLR-2 activity, thereby inhibiting or treating HSV infection in the cell.

Cells suitable for use in the methods described herein can be, e.g., mammalian cells (e.g., human or murine cells). The cells can be in culture or in a living animal (e.g., a mammal such as a mouse or human). In some embodiments, the cells are in a living mammal and the sign of HSV-1 infection is at least one symptom of encephalopathy. In some embodiments, the cell is in a neonatal mammal and the indicator of HSV infection is at least one symptom of TORCH infection, e.g., one or more of blood pressure instability, shock, fever, jaundice, hepatosplenomegaly, and the development of disseminated intravascular coagulation.

The methods can also be carried out in a test population of mammals. In such a method, the indication of HSV infection in the mammals is at least one symptom of encephalopathy or TORCH infection, such that a decrease in the severity of the symptom in the population of mammals compared to a control population of mammals indicates that the compound is a candidate compound for treating HSV infection.

Compounds suitable for use in the methods described herein can be, e.g., TLR2 antisense nucleic acids, small interfering RNAs (siRNA), or TLR2 dominant negative polypeptides (e.g., a mutated full-length TLR2, or fragment, e.g., the TLR2 extracellular binding domain). The compound can specifically bind to a TLR2 polypeptide (e.g., anti-TLR2 antibodies or TLR2-binding fragments thereof).

The invention also relates to methods of inhibiting or treating an HSV infection in a cell. The methods include the steps of providing a cell, e.g., a cell that is susceptible to HSV infection or a cell that is HSV infected, and contacting the cell with a compound that can inhibit TLR-2 expression or activity in an amount and for a time sufficient to inhibit TLR-2 expression or activity, thereby inhibiting or treating HSV infection in the cell. The HSV can be, e.g., HSV-1 or HSV-2. The cell can be in a living mammal (e.g., a mouse or a human). In certain embodiments, the mammal is a neonate, a child, or an adult.

A test compound that has been screened by a method described herein and determined to be useful in inhibiting HSV infection in a cell can be considered a candidate compound. A candidate compound that has been screened, e.g., in an in vivo model of HSV infection, e.g., in a model of HSV-TORCH syndrome or encephalitis, and determined to have a desirable effect on the disorder, e.g., on one or more symptoms of the disorder, can be considered a candidate therapeutic agent. Candidate therapeutic agents, once screened in a clinical setting, can be used as therapeutic agents. Candidate therapeutic agents and therapeutic agents can be optionally optimized and/or derivatized, and formulated with physiologically acceptable excipients to form pharmaceutical compositions.

In another aspect, the invention relates to methods of treating HSV infection in a subject. The methods include identifying a subject (e.g., a neonate, a child, or an adult) in need of treatment for HSV infection (e.g., HSV-1 or HSV-2 infection), and administering to the subject a therapeutically effective amount of a compound that decreases TLR2 expression or activity, thereby treating HSV infection in the subject. The subject can be a neonate, a child, or an adult mammal (e.g., a mouse or a human). The subject may have at least one symptom of encephalopathy or TORCH infection as described herein.

As used herein, TORCH Syndrome refers to infection of a developing fetus or newborn by any of a group of infectious agents, e.g., Toxoplasmosis, Other infections, Rubella, Cytomegalovirus, or Herpes. As used herein, "other infections" can include syphilis, hepatitis B, Coxsackie's virus, Epstein-Barr virus, varicella-zoster virus, and human parvovirus.

"HSV" infections include infection with either or both of HSV-1 or HSV-2. As used herein, "treating an HSV infection" (e.g., an HSV-1 and/or HSV-2 infection) can include ameliorating an adverse effect of HSV infection, e.g., effects on the central nervous system such as encephalitis, and/or sepsis-like symptoms of TORCH infection in neonates, e.g., as described herein. Thus, a treatment as described herein can be used to decrease the effects of HSV infection (e.g., in neonates, children, and adults).

"Polypeptide" means a chain of amino acids regardless of length or post-translational modifications. As used herein, the term "TLR2" means a TLR2 polypeptide.

For example, a TLR2 polypeptide can be a full-length TLR2 protein (e.g., Genbank accession no. NP_003255) (gene NM_003264; human TLR2) or AAH14693 (gene NM 011905; murine TLR2), and are hereby incorporated by reference in their entirety. A "dominant negative" TLR2 is a TLR2 variant polypeptide that, when co-expressed with a functional TLR2, significantly decreases the activity of the functional TLR2.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of the polypeptide having less than about 30% (by dry weight), e.g., about 20%, 10%, or 5%, of other polypeptides (also referred to herein as a "contaminating protein"), or of chemical precursors or chemicals. When the polypeptide or biologically active portion thereof is recombinantly produced, it is also generally substantially free of culture medium, i.e., culture medium represents less than about 20% of the volume of the protein preparation, e.g., less than about 10%, or 5%.

As used herein, a "biologically active portion" of a TLR2 includes a fragment of a TLR2 protein that has at least one biological activity of a naturally occurring TLR2, e.g., the fragment can participate in an interaction between a TLR2 molecule and a molecule that is a naturally occurring binding partner (ligand) of TLR2, can activate a transcription factor (e.g., Nuclear Factor-kappa B (NF-κB)), and/or can induce or increase chemokine secretion or cytokine secretion (e.g., secretion of one or more of IL-1, IL-6, IL-8, Tumor Necrosis Factor (TNF), Monocyte Chemoattractant Protein-1 (MCP-1), and/or Macrophage Inflammatory Protein-I (MIP-1)). Biologically active portions of a TLR2 protein include polypeptides comprising amino acid sequences sufficiently homologous to or derived from the amino acid sequence of a TLR2 protein, which include fewer amino acids than the full length TLR2 protein, and exhibit at least one activity of a TLR2 protein (e.g., binding to a TLR2 ligand, e.g., HSV). Typically, biologically active portions comprise a domain (e.g., an extracellular domain) or motif with at least one activity of the TLR2 protein, e.g., a domain or motif capable of binding to a TLR2 ligand such as zymosan. A biologically active portion of a TLR2 protein can be a polypeptide that is, for example, 10 or more amino acids in length, e.g., about 25, 50, 100, 200 or more amino acids. Biologically active portions of a TLR2 protein can be used as targets for developing agents that modulate a TLR2-mediated activity, e.g., a biological activity described herein such as decreasing the deleterious effects of HSV-1 infection in a neonate.

TLR2 and fragments thereof, and derivatives and other variants of a TLR2 sequence are collectively referred to as "TLR2 polypeptides." Nucleic acid molecules encoding such polypeptides or proteins are collectively referred to as "TLR2 nucleic acids." "TLR2 molecules" refers to TLR2 nucleic acids, polypeptides, and TLR2 antibodies (antibodies that specifically bind to a TLR2).

As used herein, the term "nucleic acid molecule" includes DNA molecules (e.g., a cDNA or genomic DNA), RNA molecules (e.g., an mRNA), and analogs of the DNA or RNA generated, e.g., by the use of nucleotide analogs. The nucleic acid molecule can be single-stranded or double-stranded.

The term "isolated and purified nucleic acid molecule" includes nucleic acid molecules that are separated from other nucleic acid molecules that are present in the natural source of the nucleic acid. In general, such sequences are separated from flanking genes. When the nucleic acid molecule is from a synthetic source, such a molecule is in a substantially homogeneous preparation with respect to sequence. A substantially homogeneous preparation has less than 10%, e.g., less than 5%, or less than 1%, contaminating sequence.

A molecule that specifically binds to a second molecule is one that binds to the second molecule, but does not substantially bind to other molecules in a sample, e.g., a biological sample that naturally contains the second molecule. For example, a molecule that specifically binds to TLR2 is a molecule that binds to a TLR2, but does not substantially bind other molecules in a sample, e.g., a biological sample, that contains the TLR2.

"Subject," as used herein, refers to a mammal, e.g., a human, or an experimental, animal, or disease model. The subject can be a non-human animal, e.g., a mouse, rat, dog, horse, cow, goat, or other domestic animal.

A "neonate" is a subject that is approximately less than one month old. For example, a human neonate is about 28 days or less after birth. In the case of a prematurely delivered infant, the infant is a neonate up to and including 28 days from its predicted birth date. In some embodiments, a neonate is less than a week old. A neonatal mouse is up to and including 3 weeks old. In general, a subject that was infected with HSV (e.g., HSV-1 or HSV-2) during the neonatal period exhibits at least one symptom of neonatal HSV infection during the neonatal period. Thus, treatment of or use of a neonate (e.g., in a method described herein) infected with HSV means that the neonate was infected with HSV during the neonatal period, although the treatment or use of the neonate may extend beyond the neonatal period.

As used herein, a "therapeutically effective" amount or dose refers to that amount of a compound sufficient to result in amelioration of at least one symptom of HSV infection. Such symptoms are described herein and known in the art (for example, see Berkow et al., *The Merck Manual*, Merck Research Laboratories, Rahway, N.J., 1992).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIGS. 6A-C are micrographs of meninges illustrating mononuclear cell infiltrates in wild type and TLR4 knockouts. The meninges of TLR2 knockout mice was normal. FIGS. 6D-F are micrographs of cerebellum demonstrating the presence of mononuclear cell infiltrates and activated glial cells in wild type and TLR4 knockouts. The cerebellar tissue from TLR2 knockout mice was normal. FIGS. 6G-I are micrographs illustrating blood vessels with accumulating mononuclear cells along the endothelial surface as well as perivascular cuffing in wild type and TLR4 knockout brain. Blood vessels in the brains of TLR2 knockout mice were normal with no evidence of inflammatory mononuclear cell accumulation.

DETAILED DESCRIPTION

Figure 1A:
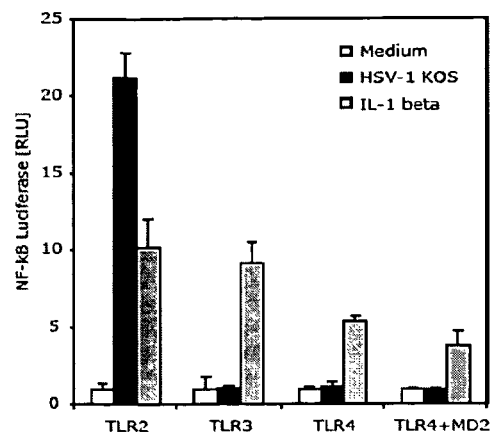
FIG. 1A is a bar graph depicting the results of experiments in which human embryonic kidney cells (HEK293) expressing human TLR2, TLR3, or TLR4±MD2 were transfected with an NF-κB-driven firefly luciferase reporter plasmid and stimulated for six hours with herpes simplex virus 1 (KOS strain) at a multiplicity of infection (MOI) of 100 or with IL-1β (100 ng/ml) as a positive control. Luciferase activity was calculated in RLU (relative luciferase units) as a ratio of NF-κB-dependent firefly luciferase activity to NF-κB independent *Renilla luciferase* activity. The results are shown as the mean±SD of triplicate wells. Each cell line was tested in 3-10 independent experiments.

It is demonstrated herein that TLR2 mediates the inflammatory cytokine response to HSV-1, and is responsible for severe symptoms that are associated with HSV infection in neonates and adults. Loss-of-function studies with macrophages demonstrated an essential role for TLR2 in the production of inflammatory cytokines after HSV-1 challenge, while gain-of-function studies demonstrated that expression of TLR2 in HEK293 cells was sufficient to confer responsiveness to HSV-1. Consistent with the role of TLR2 in the HSV-1-induced inflammatory response, infection with HSV-1 induced a blunted cytokine response in TLR2$^{-/-}$ mice compared to wild type or TLR4$^{-/-}$ mice both in the serum and within the brain. This attenuated cytokine response was paralleled by a reduction in symptoms of encephalitis in TLR2$^{-/-}$ mice, as compared to wild type and TLR4$^{-/-}$ mice.

HSV-1 infected TLR2$^{-/-}$ neonatal mice developed mild symptoms, and mortality was less than 40% over a 21 day period. In contrast, wild type and TLR4$^{-/-}$ neonates rapidly succumbed to HSV-1 infection with >90% mortality by day 6. Thus, surprisingly, the data provided herein demonstrate that the TLR2-mediated cytokine response to HSV-1 is not protective, but rather is detrimental to the host, particularly within the brain.

The reasons for the large discrepancy between the response to HSV infection in neonatal animals (and humans) and adults has not previously been established. The data provided herein demonstrate that neonatal susceptiblity is TLR2-dependent. It has been suggested that the poor outcomes associated with infection in neonates is due to some failure of the immature immune system to contain the virus. The findings disclosed herein demonstrate that rather than being less responsive than adults, the neonatal response to viral antigens, in which the innate immune response is through TLR2, is stronger than those seen in adults.

The surprising finding that TLR2 deficient mice are less likely to die of HSV-1 challenge than wild type mice demonstrates that neonatal animals, rather than being less able to contain the virus, die at least in part, because of their exuberant cytokine responses to viral antigens. Thus, drugs or other therapies that dampen the innate immune response (e.g., the innate immune response that is mediated by TLR2 signaling) will decrease morbidity and mortality caused by HSV (e.g., HSV-1 or HSV-2 infection in neonates, children, and adults).

Accordingly, the new methods described herein relate to the identification of compounds that are useful for treating HSV infection (e.g., HSV-1 and HSV-2 infection), including adverse effects of infection on the central nervous system such as encephalitis, and symptoms of TORCH syndrome in neonates. Thus, the methods relate to identifying compounds that both decrease TLR2 expression or activity (e.g., by binding to TLR2) and that decrease the effects of HSV infection (e.g., in neonates, children, and adults). Compounds identified using such methods are useful for treating subjects at risk of HSV infection or subjects infected with HSV.

Screening Assays

In part, the new methods include screening assays for the identification of compounds that decrease TLR2-mediated signaling for use in the treatment of HSV infection. Such compounds can be identified from information that may be available in the art, or using laboratory methods for identifying modulators, i.e., test compounds or agents (e.g., proteins, peptides, peptidomimetics, peptoids, small inorganic molecules, small non-nucleic acid organic molecules, nucleic acids (e.g., anti-sense nucleic acids, siRNA, oligonucleotides, synthetic oligonucleotides), or other drugs) that inhibit TLR2 signaling, in particular, TLR2 signaling that is associated with HSV infection, e.g., in a neonate. For example, such a compound may bind to a TLR2 polypeptide and have an inhibitory effect on indicators of HSV infection that are associated with TLR2 signaling, e.g., by inhibiting expression or activity of TLR2. Compounds thus identified can be used to modulate the effects of HSV-1 infection, for example, in a neonate in a therapeutic protocol. Such compounds are also useful to elaborate the biological function of TLR2.

In some cases, an assay involves the identification of a compound that inhibits TLR2 expression or activity, and determining whether the compound can decrease one or more undesirable effects of HSV infection in a cell or in a subject. Methods of identifying a compound that inhibits expression or activity of TLR2 are known in the art and described herein. Compounds previously identified as able to inhibit the expression or activity of a TLR2 can also be used in certain methods.

In some cases, an assay for identifying an inhibitor of TLR2 expression or activity is a cell-based assay in which a cell that expresses a TLR2 protein or biologically active portion thereof is contacted with a test compound, and the ability of the test compound to modulate TLR2 activity is determined. Determining the ability of the test compound to modulate TLR2 activity can be accomplished by monitoring, for example, IL-6 activity. The cell, for example, can be of mammalian origin, e.g., murine or human. In general, useful cell types are those that can be infected with HSV (e.g., HSV-1 or HSV-2).

The ability of the test compound to modulate TLR2 binding to a TLR2 ligand, or to bind to TLR2 can also be evaluated. A number of TLR2 ligands are known in the art and include LTA (lipoteichoic acids), zymosan, peptidoglycan, ara-lipoarabinomannan, and human cytomegalovirus. TLR2 co-receptors are known in the art and include TLR1 and TLR6. Such compounds can then be tested for their ability to inhibit expression or activity (e.g., activation of one or more components of the TLR2 signaling pathway such as IL-6 and NF-κB).

A compound that binds to TLR2 can be identified, for example, by coupling the compound with a radioisotope or enzymatic label such that binding of the compound to TLR2 can be determined by detecting the labeled compound in a complex. Alternatively, a component of the assay can be coupled with a radioisotope or enzymatic label to monitor the ability of a test compound to modulate TLR2 binding to a TLR2 ligand in a complex. For example, a compound can be labeled with $^{125}$I, $^{35}$S, $^{14}$C, or $^3$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound to interact with TLR2, with or without the labeling of any of the interactants, can be evaluated. For example, a microphysiometer can be used to detect the interaction of a compound with TLR2 without the labeling of either the compound or the TLR2 (McConnell et al., Science 257: 1906-1912 (1992)). As used herein, a "microphysiometer" (e.g., Cytosensor®) is an analytical instrument that measures the rate at which a cell acidifies its environment using a light-addressable potentiometric sensor (LAPS). Changes in this acidification rate can be used as an indicator of the interaction between a compound and TLR2.

A cell-free assay is also provided in which a TLR2 protein or biologically active portion thereof is contacted with a test compound and the ability of the test compound to bind to the TLR2 protein or biologically active portion thereof is evaluated. In general, biologically active portions of the TLR2 polypeptides to be used in assays include fragments that participate in interactions with non-TLR2 molecules, e.g., fragments with high surface probability scores.

Soluble and/or membrane-bound forms of isolated proteins (e.g., a TLR2 polypeptide) can be used in the cell-free assays. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of a TLR2 polypeptide and the test compound under conditions and for a time sufficient to allow the two components to interact and bind, thus forming a complex that can be removed and/or detected. In some assays, the ability of a test compound to inhibit the binding between a TLR2 polypeptide and a TLR2 ligand is determined.

The interaction between two molecules can also be detected, e.g., using fluorescence energy transfer (FET) (for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of a TLR2 polypeptide to bind to a target molecule can be accomplished using real-time Biomolecular Interaction Analysis (BIA) (e.g., Sjolander et al., Anal. Chem. 63: 2338-2345 (1991) and Szabo et al., Curr. Opin. Struct. Biol. 5: 699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the TLR2 or the test substance is anchored onto a solid phase. The TLR2/test compound complexes anchored on the solid phase can be detected at the end of the reaction. Generally, the target gene product is anchored onto a solid surface, and the test compound (which is not anchored) can be labeled, either directly or indirectly, with detectable labels discussed herein.

It may be desirable to immobilize TLR2 polypeptide, an anti-TLR2 antibody, or a TLR2 binding molecule (e.g., a TLR2 ligand) to facilitate separation of complexed from uncomplexed forms of one or both of the proteins, as well as to accommodate automation of the assay. Binding of a test compound to a TLR2 polypeptide, or interaction of a TLR2 polypeptide with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided, which adds a domain that allows one or both of the proteins to be bound to a matrix. For example, glutathione-S-transferase/TLR2 fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed TLR2 binding molecule or TLR2 polypeptide, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of TLR2 binding or activity determined using standard techniques.

Other techniques for immobilizing either a TLR2 protein or a target molecule on matrices include using conjugation of biotin and streptavidin. Biotinylated TLR2 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In some cases, the assay is performed utilizing antibodies reactive with TLR2 polypeptide or ligand, but which do not interfere with binding of the TLR2 polypeptide to the ligand. Such antibodies can be derivatized to the wells of the plate, and unbound ligand or TLR2 polypeptide trapped in the wells by antibody conjugation. Methods for detecting such complexes, in addition to those described above for the GST-immobilized complexes, include immunodetection of complexes using antibodies reactive with the TLR2 polypeptide or ligand, as well as enzyme-linked assays which rely on detecting an enzymatic activity associated with the TLR2 polypeptide or ligand.

Alternatively, cell-free assays can be conducted in a liquid phase. In such an assay, the reaction products are separated from unreacted components, by any of a number of known techniques, including but not limited to: differential centrifugation (see, for example, Rivas and Minton, *Trends Biochem Sci* 18: 284-7 (1993)); chromatography (gel filtration chromatography, ion-exchange chromatography); electrophoresis (see, e.g., Ausubel et al., eds. *Current Protocols in Molecular Biology* 1999, J. Wiley: New York.); and immunoprecipitation (see, for example, Ausubel et al., eds., 1999, *Current Protocols in Molecular Biology*, J. Wiley: New York). Such resins and chromatographic techniques are known to one skilled in the art (e.g., Heegaard, J. Mol. Recognit., 11: 141-148 (1998); Hage et al., J. Chromatogr. B. Biomed. Sci. Appl., 699: 499-525 (1997)). Further, fluorescence energy transfer may also be conveniently utilized, as described herein, to detect binding without further purification of the complex from solution.

The assay can include contacting the TLR2 polypeptide with a known compound that binds to TLR2 to form an assay mixture, contacting the assay mixture with a test compound, and determining the ability of the test compound to interact with a TLR2 polypeptide, e.g., by determining the ability of the test compound to preferentially bind to TLR2 or a biologically active portion thereof, or to modulate the activity of TLR2, as compared to the known compound.

Useful assays also include methods for determining the ability of the test compound to modulate the activity of a TLR2 protein through binding to the TLR2 or by modulation of the activity of a downstream effector of a TLR2 target molecule, e.g., NF-κB. For example, the activity of the effector molecule on an appropriate target can be determined, or the binding of the effector to an appropriate target can be determined, as previously described.

To identify compounds that interfere with the interaction between TLR2 and its cellular (e.g., co-receptors) or extracellular (e.g., ligands) binding partner(s), a reaction mixture containing the TLR2 and the binding partner is prepared, under conditions and for a time sufficient, to allow the two products to form complex. To test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the TLR2 polypeptide and the cellular or extracellular binding partner is then detected. The formation of a complex in the control reaction, but not in the reaction mixture containing the test compound, indicates that the compound interferes with the interaction of the TLR2 polypeptide and the interactive binding partner.

Another method of identifying compounds that are effective for treating HSV infection in a subject is to determine the effect of the compound on TLR2 activity, e.g., by assaying production of inflammatory cytokines or chemokines (e.g., IL-1, IL-6, IL-8, MCP-1, MIP-1, and/or TNF), or the activation of gene expression, e.g., by NF-κB, in a cell expressing functional TLR2 (and, in some cases, infected with HSV), in the presence of the test compound. Methods for performing such assays are known in the art; some are described herein. Test compounds that reduce TLR2 activity, e.g., as compared to TLR2 activity in a reference, e.g., a control in the absence of the test compound, can be considered effective compounds for the treatment of a subject infected with HSV. An effective compound is expected, in an HSV-1 infected subject, to decrease levels of inflammatory cytokines that are induced by the TLR2 signaling pathway as compared to the levels of inflammatory cytokines that are induced in a subject that was not treated with the compound, thereby reducing the negative effects of HSV infection. Similarly, a compound that is useful for treating TLR2-mediated effects of HSV infection will inhibit the induction of inflammatory cytokines associated with activation of the TLR2 signaling pathway in a cell that is infected with HSV and contacted with the compound compared to a control cell that was not contacted with the compound.

The assays described herein can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the TLR2 polypeptide and a binding partner (e.g., a TLR2 ligand), e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. Examples of the various formats are briefly described below.

In a heterogeneous assay system, either the TLR2 or the interactive cellular or extracellular binding partner is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In some cases, a homogeneous assay can be used. For example, a preformed complex of a TLR2 polypeptide and the interactive cellular or extracellular binding partner of TLR2 is prepared in that either the TLR2 or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt TLR2-binding partner interaction can be identified.

Compounds

The test compounds used in the methods described herein can include those obtained using any of the numerous approaches in combinatorial library methods known in the art, including: biological libraries (e.g., peptides, polypeptides, or nucleic acids); peptoid libraries (libraries of molecules having the functionalities of peptides, but with a novel, non-peptide backbone which are resistant to enzymatic degradation but which nevertheless remain bioactive; e.g., Zuckermann et al., J. Med. Chem., 37: 2678-2685 (1994)); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer, or small molecule libraries of compounds (Lam, Anticancer Drug Des. 12: 145 (1997)).

Examples of methods for the synthesis of molecular libraries can be found in the art, for example in: DeWitt et al., Proc. Natl. Acad. Sci. USA, 90: 6909 (1993); Erb et al., Proc. Natl. Acad. Sci. USA, 91: 11422 (1994); Zuckermann et al., J. Med. Chem., 37: 2678 (1994); Cho et al., Science, 261: 1303 (1993); Carrell et al., Angew. Chem. Int. Ed. Engl., 33: 2059 (1994); Carell et al., Angew. Chem. Int. Ed. Engl., 33: 2061 (1994); and in Gallop et al., J. Med. Chem., 37: 1233 (1994). Libraries of compounds can be presented in solution (e.g., Houghten, Biotechniques, 13: 412-421 (1992)), or on beads (Lam, Nature, 354: 82-84 (1991)), chips (Fodor, Nature, 364: 555-556 (1993)), bacteria (Ladner, U.S. Pat. No. 5,223,409), spores (Ladner, U.S. Pat. No. 5,223,409), plasmids (Cull et al., Proc. Natl. Acad. Sci. USA, 89: 1865-1869 (1992)), or on phage (Scott and Smith, Science, 249: 386-390 (1990); Devlin, Science, 249: 404-406 (1990); Cwirla et al., Proc. Natl. Acad. Sci. USA, 87: 6378-6382 (1990); Felici, J. Mol. Biol., 222: 301-310 (1991); Ladner supra).

TLR2 Polypeptides

In some cases, the new methods employ an isolated TLR2 polypeptide (a full-length TLR2 protein or a variant, e.g., a mutant or fragment, thereof), e.g., a biologically active portion such as an extracellular domain. Variants, both artificial and naturally-occurring, of TLR2 can be used (for example, a TLR2 polypeptide having one or more conservative amino acid substitutions). TLR2 polypeptides are useful as described herein, for example, as immunogens or antigens to raise or test (or more generally to bind) anti-TLR2 antibodies (e.g., antigenic fragments of TLR2), or to serve as inhibitory compounds (e.g., TLR2 dominant negatives). Such polypeptides can be isolated from cells or tissue sources using standard protein purification techniques.

A TLR2 polypeptide can be isolated from a natural source, can be produced by recombinant DNA methods, or can be synthesized chemically. Examples of TLR2 polypeptides include polypeptides consisting of the amino acid sequences of Genbank Accession Nos. NP_003255 (gene NM_003264; human TLR2) and AAH14693 (gene NM_011905; murine TLR2), and are hereby incorporated by reference in their entirety. In some cases, a TLR2 polypeptide includes an amino acid sequence that has at least 80% sequence identity with a known TLR2 polypeptide, e.g., at least 85%, 90%, 95% or more identity, and has at least one biological activity of a known TLR2 (e.g., can bind to a naturally-occurring TLR2 ligand or co-receptor, can induce activation of gene transcription (e.g., via NF-κB), or induce secretion of a chemokine or cytokine, e.g., IL_1, IL-6, IL-8, TNF, MCP-1, or MIP-1). Naturally-occurring TLR2 ligands and co-receptors include TLR1, TLR6, zymosan, peptidoglycan, lipotechoic acid, and ara-lipoarabinomannan.

Variants of TLR2 polypeptide useful in methods described herein can also include fragments including at least an extracellular binding domain of the TLR2 or a mutant thereof. Such fragments have been shown to have inhibitory activity, see, e.g., LeBouder et al., J. Immunol., 171: 6680-9 (2003). Additional useful polypeptide fragments can be identified, e.g., by the ability to compete with full length TLR2 for binding of a TLR2 ligand (e.g., HSV). Variants of naturally occurring TLR2 amino acid sequences can be tested for their ability to inhibit TLR2 activity, e.g., signaling that is associated with HSV infection. Other appropriate sequences besides those described herein are known in the art and can be used in the methods disclosed herein.

TLR2 dominant negative polypeptides (i.e., polypeptides whose expression significantly inhibits the activity of wild-type, e.g., endogenous, TLR2) are also useful in the methods described herein. Dominant negatives, and methods for making and testing them, are known in the art. Examples of TLR2 dominant negative polypeptides include fragments and deletion mutants, e.g., less than the full-length TLR2, that are useful in the methods described herein. Dominant negative polypeptides typically encompass the extracellular domain of a TLR2 (e.g., a polypeptide including about amino acids 1-587), and can include TLR2 deletion mutants lacking the conserved intracellular Toll/Interleukin-1 receptor (TIR) domain (e.g., a polypeptide including amino acids 1-642), (see, e.g., Sandor et al., J. Cell Biol. 162 (6): 1099-1110 (2003); Xu et al., Nature 408 (6808): 111-5 (2000)) or the amino acids from Ser40-Ile64 (Fujita et al., J. Immunol. 171 (7): 3675-83 (2003)), e.g., of Genbank accession no. NP_003255 (gene NM_003264; human TLR2) or AAH 14693 (gene NM_011905; murine TLR2), and are hereby incorporated by reference in their entirety. Dominant negative mutants can include point mutants, e.g., the P681H (Xu et al., 2000, supra), L107E, L112E, and L115E mutants (Fujita et al., 2003, supra).

As used herein, "conservative amino acid substitution" means a substitution of an amino acid in a polypeptide within an amino acid family. Families of amino acids are recognized in the art and are based on physical and chemical properties of the amino acid side chains. Families include the following: amino acids with basic side chains (e.g., lysine, arginine, and histidine); amino acids with acidic side chains (e.g., aspartic acid and glutamic acid); amino acids with uncharged polar side chains (e.g., glycine, asparagine, glutamine, serine, threonine, tyrosine, and cysteine); amino acids with nonpolar side chains (e.g., alanine, valine, leucine, isoleucine, proline, phenylalanine, methionine, and tryptophan); amino acids with branched side chains (e.g., threonine, valine, and isoleucine); and amino acids with aromatic side chains (e.g., tyrosine, phenylalanine, tryptophan, and histidine). An amino acid can belong to more than one family.

Antibodies

In another aspect, antibodies are provided that are anti-TLR2 antibodies (also referred to as TLR2 antibodies). The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which can be generated by treating the antibody with an enzyme such as pepsin.

The antibody can be a polyclonal, monoclonal, monospecific, recombinant, e.g., a chimeric or humanized, fully human, non-human, e.g., murine, or single chain antibody. In some cases, the antibody has effector function and can fix complement. The antibody can be coupled to a toxin or imaging agent.

A full-length TLR2 protein or antigenic peptide fragment of a TLR2 can be used as an immunogen or can be used to identify anti-TLR2 antibodies (TLR2 antibodies) made with other immunogens, e.g., cells, membrane preparations, and the like. The antigenic peptide of a TLR2 polypeptide should include at least 8 amino acid residues of a TLR2 protein. In general, the polypeptide will encompass an epitope of TLR2, e.g., an extracellular domain. The antigenic peptide can include at least 10 amino acid residues, at least 15 amino acid residues, at least 20 amino acid residues, or at least 30 amino acid residues.

Fragments of a TLR2, e.g., fragments that include the extracellular domain, e.g., about residues 1-587 of NP_003255 (human TLR2) or of AAH14693 (murine TLR2), can also be used to make an antibody against an extracellular region of the TLR2. Epitopes encompassed by the antigenic peptide are generally regions of TLR2 that are located on the surface of the protein, e.g., hydrophilic regions, as well as regions with high antigenicity. For example, an Emini surface probability analysis of the human TLR2 protein sequence can be used to indicate the regions that have a particularly high probability of being localized to the surface of the TLR2 protein and are thus likely to constitute surface residues useful for targeting antibody production.

In some embodiments, the antibody can bind to the extracellular portion of the TLR2 protein, e.g., it can bind to a whole cell that expresses the TLR2 protein. In another embodiment, the antibody binds to an intracellular portion of the TLR2 protein.

Chimeric, humanized, e.g., completely human, antibodies are desirable for applications that include repeated administration, e.g., therapeutic treatment (and some diagnostic applications) of a human subject.

The anti-TLR2 antibody can be a single chain antibody. A single-chain antibody (scFV) may be engineered (see, for example, Colcher et al., Ann. N.Y. Acad. Sci. 880: 263-80 (1999); and Reiter, Clin. Cancer Res. 2: 245-52 (1996)). The single chain antibody can be dimerized or multimerized to generate multivalent antibodies having specificities for different epitopes of the same target TLR2 protein.

In some cases, the antibody has reduced or no ability to bind to an Fc receptor. For example, the antibody can be an isotype or subtype, fragment or other mutant, which does not support binding to an Fc receptor, e.g., it has a mutagenized or deleted Fc receptor binding region.

An anti-TLR2 antibody (e.g., monoclonal antibody) can be used in methods of inhibiting TLR2 signaling associated with HSV infection. Such antibodies can also be used to monitor TLR2 protein levels or localization in cells or tissue as part of a screening procedure to identify compounds that inhibit TLR2 expression or activity (e.g., during HSV infection). Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

When fragments of an antibody are used, the smallest inhibitory fragment that binds to the target antigen (e.g., TLR2) can be used. For example, peptides having an amino acid sequence corresponding to the Fv region of the antibody can be used.

In some embodiments, the antibody is an inhibitory antibody, e.g., the antibody can significantly inhibit the activity of TLR2. Inhibitory antibodies are known in the art, e.g., as described in Sandor et al., 2003, supra, and Meng et al., J. Clin. Inv. 113 (10): 1473-1481 (2004).

Antisense Nucleic Acid Molecules, Ribozymes, siRNA, and Modified Nucleic Acid Molecules Compounds useful in the new methods include isolated nucleic acid molecules that are antisense to TLR2, or other nucleic acid molecules that can inhibit TLR2 transcription, processing, or translation. An antisense nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire TLR2 coding strand, or to only a portion thereof (e.g., the coding region of human TLR2). In some cases, the antisense nucleic acid molecule is antisense to a "noncoding region" of the coding strand of a nucleotide sequence encoding TLR2 (e.g., the 5' and 3' untranslated regions).

An antisense nucleic acid can be designed such that it is complementary to the entire coding region of TLR2 mRNA or a portion thereof. In general, the antisense molecule is an oligonucleotide that is antisense to only a portion of the coding or noncoding region of TLR2 mRNA. For example, the antisense oligonucleotide can be complementary to the region surrounding the translation start site of TLR2 mRNA, e.g., between the −10 and +10 regions of the target gene nucleotide sequence of interest. An antisense oligonucleotide can be, for example, about 20, 25, 30, 35, 40, 45, 50, 55, 60, 65, 70, 75, 80, or more nucleotides in length. Based upon sequences known in the art and disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

An antisense nucleic acid can be constructed using chemical synthesis and enzymatic ligation reactions using procedures known in the art. For example, an antisense nucleic acid (e.g., an antisense oligonucleotide) can be chemically synthesized, e.g., using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The new antisense nucleic acid molecules are typically administered to a subject (e.g., by direct injection at a tissue site), or generated in situ (e.g., using an expression vector that contains a sequence encoding the antisense molecule) such that they hybridize with or bind to cellular mRNA and/or genomic DNA encoding a TLR2 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are generally used.

In some cases, the antisense nucleic acid molecule can be an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids., Res. 15: 6625-6641 (1987)). The antisense nucleic acid molecule can also comprise a 2'-o-methylribonucleotide (Inoue et al., Nucleic Acids Res., 15: 6131-6148 (1987)) or a chimeric RNA-DNA analogue (Inoue et al., FEBS Lett., 215: 327-330 (1987)).

Another antisense nucleic acid that is useful in the methods described herein is a ribozyme. A ribozyme having specificity for a TLR2-encoding nucleic acid can include one or more sequences complementary to the nucleotide sequence of a TLR2 cDNA, and a sequence having known catalytic sequence responsible for mRNA cleavage (see U.S. Pat. No. 5,093,246 or Haselhoff and Gerlach, 1988, Nature, 334: 585-591). For example, a derivative of a *Tetrahymena* L-19 IVS RNA can be constructed in which the nucleotide sequence of the active site is complementary to the nucleotide sequence to be cleaved in a TLR2-encoding mRNA (e.g., Cech et al., U.S. Pat. No. 4,987,071; and Cech et al., U.S. Pat. No. 5,116,742. Alternatively, TLR2 mRNA can be used to select a catalytic RNA having a specific ribonuclease activity from a pool of RNA molecules (e.g., Bartel and Szostak, Science, 261: 1411-1418 (1993)).

In some embodiments, the antisense nucleic acid is a morpholino oligonucleotide (see, e.g., Heasman, Dev. Biol., 243: 209-14 (2002); Iversen, Curr. Opin. Mol. Ther., 3: 235-8 (2001); Summerton, Biochim. Biophys. Acta., 1489: 141-58 (1999).

TLR2 gene expression can be inhibited by targeting nucleotide sequences complementary to the regulatory region of the TLR2 (e.g., the TLR2 promoter and/or enhancers) to form triple helical structures that prevent transcription of the TLR2 gene in target cells (e.g., Helene, Anticancer Drug Des., 6: 569-84 (1991); Helene, Ann. N.Y. Acad. Sci., 660: 27-36 (1992); and Maher, Bioassays, 14: 807-15 (1992)). The potential sequences that can be targeted for triple helix formation can be increased by creating a so-called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

A TLR2 nucleic acid molecule can be modified at the base moiety, sugar moiety, or phosphate backbone to improve, e.g., the stability, hybridization, or solubility of the molecule. For example, the deoxyribose phosphate backbone of the nucleic acid molecules can be modified to generate peptide nucleic acids (see Hyrup et al., Bioorganic & Medicinal Chemistry, 4: 5-23 (1996)). As used herein, the terms "peptide nucleic acid" or "PNA" refer to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described, e.g., in Hyrup et al., 1996, supra and Perry-O'Keefe et al., Proc. Natl. Acad. Sci. USA, 93: 14670-675 (1996).

PNAs of TLR2 nucleic acid molecules can be used in therapeutic and diagnostic applications. For example, PNAs can be used as antisense or antigene agents for sequence-specific modulation of gene expression by, for example, inducing transcription or translation arrest or inhibiting replication. Such compounds are useful for treating undesirable TLR2-mediated effects that result from HSV infection.

In other embodiments, the oligonucleotide can include other appended groups such as peptides (e.g., for targeting host cell receptors in vivo), or agents facilitating transport across the cell membrane (e.g., Letsinger et al., Proc. Natl. Acad. Sci. USA, 86: 6553-6556 (1989); Lemaitre et al., Proc. Natl. Acad. Sci. USA, 84: 648-652 (1987); PCT Publication No. WO88/09810) or the blood-brain barrier (e.g., PCT Publication No. WO89/10134). In addition, oligonucleotides can be modified with hybridization-triggered cleavage agents (e.g., Krol et al., Bio-Techniques, 6: 958-976 (1988)) or intercalating agents (e.g., Zon, Pharm. Res., 5: 539-549 (1988)). To this end, the oligonucleotide may be conjugated to another molecule, (e.g., a peptide, hybridization triggered cross-linking agent, transport agent, or hybridization-triggered cleavage agent).

Molecular beacon oligonucleotide primer and probe molecules having at least one region which is complementary to a TLR2 nucleic acid and two complementary regions, one having a fluorophore and one a quencher, such that the molecular beacon is useful for quantitating the presence of TLR2 nucleic acid in a sample, can also be used. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

In some cases, the oligonucleotide is a small interfering RNA (siRNA) that is directed against a TLR2. These double stranded RNA (dsRNA) molecules generally comprise 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro from a DNA template, or in vivo from, e.g., small hairpin RNA (shRNA). Methods of selecting siRNA sequences and preparing them are known in the art, and commercial sources are available for such identification and synthesis (e.g., Dharmacon, Lafayette, Colo.; Ambion, Austin, Tex.; Quigen, Inc., Valencia, Calif.).

Negative control siRNAs should have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The nucleic acid compositions that are useful in the methods described herein include both siRNA and crosslinked siRNA derivatives. Crosslinking can be employed to alter the pharmacokinetics of the composition, for example, to increase half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3'OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev., 47: 99-112 (2001) (describes nucleic acids loaded to polyalkylcyanoacrylate (PACA) nanoparticles); Fattal et al., J. Control Release, 53: 137-43 (1998) (describes nucleic acids bound to nanoparticles); Schwab et al., Ann. Oncol. 5 Suppl., 4: 55-8 (1994) (describes nucleic acids linked to intercalating agents, hydrophobic groups, polycations or PACA nanoparticles); and Godard et al., Eur. J. Biochem., 232: 404-10 (1995) (describes nucleic acids linked to nanoparticles).

The nucleic acid molecules can also be labeled using methods known in the art. For example, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

Delivery of Oligonucleotides for Longer-Term Expression

Synthetic siRNAs or other oligonucleotides or nucleic acids described herein can be delivered into cells by cationic liposome transfection and electroporation. In general, exogenous siRNAs only show short-term persistence of the silencing effect (about 4-5 days). Several strategies for expressing siRNA duplexes within cells from recombinant DNA constructs allow longer-term target gene suppression in cells, including mammalian Pol III promoter systems (e.g., HI or U6/snRNA promoter systems (Tuschl, Nature Biotechnol., 20: 440-448 (2002)) capable of expressing functional double-stranded siRNAs; (Bagella et al., J. Cell. Physiol., 177: 206-213 (1998); Lee et al., Nature Biotechnol., 20: 500-505 (2002); Miyagishi et al., Nucleic Acids Res. Suppl., 2: 113-114 (2002); Paul et al., Nature Biotechnol., 20: 505-508 (2002); Yu et al., Proc. Natl. Acad. Sci. USA, 99 (9): 6047-6052 (2002); Sui et al., Proc. Natl. Acad. Sci. USA, 99 (6): 5515-5520 (2002)). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by HI or U6 snRNA promoter and expressed in cells, can inhibit target gene expression. Constructs containing siRNA sequence under the control of T7 promoter also make functional siRNAs when cotransfected into the cells with a vector expression T7 RNA polymerase (Jacque, Nature, 418: 435-438 (2002)).

Animal cells express a range of noncoding RNAs of approximately 22 nucleotides termed micro RNA (mRNAs) and can regulate gene expression at the post transcriptional or translational level during animal development. One common feature of mRNAs is that they are all excised from an approximately 70 nucleotide precursor RNA stem-loop, probably by Dicer, an RNase III-type enzyme, or a homolog thereof. By substituting the stem sequences of the mRNA precursor with mRNA sequence complementary to the target mRNA, a vector construct that expresses the novel mRNA can be used to produce siRNAs to initiate RNAi against specific mRNA targets in mammalian cells (Zeng, Mol. Cell, 9: 1327-1333 (2002)). When expressed by DNA vectors containing polymerase III promoters, micro-RNA designed hairpins can silence gene expression (McManus, 2002, supra). Viral-mediated delivery mechanisms can also be used to induce specific silencing of targeted genes through expression of siRNA, for example, by generating recombinant adenoviruses harboring siRNA under RNA Pol II promoter transcription control (Xia et al., Nat. Biotechnol., 20: 1006-1010 (2002)). Infection of HeLa cells by such recombinant adenoviruses allows for diminished endogenous target gene expression. Injection of the recombinant adenovirus vectors into transgenic mice expressing the target genes of the siRNA results in in vivo reduction of target gene expression (id). In an animal model, whole-embryo electroporation can efficiently deliver synthetic siRNA into post-implantation mouse embryos (Calegari et al., Proc. Natl. Acad. Sci. USA, 99: 14236-14240 (2002)). In adult mice, efficient delivery of siRNA can be accomplished by "high-pressure" delivery technique, a rapid injection (within 5 seconds) of a large volume of siRNA containing solution into animal via the tail vein (Liu, Gene Ther., 6: 1258-1266 (1999); McCaffrey, Nature, 418: 38-39 (2002); Lewis, Nature Genetics, 32: 107-108 (2002)). Nanoparticles and liposomes can also be used to deliver siRNA into animals.

Uses of Engineered RNA Precursors to Induce RNAi

Engineered RNA precursors, introduced into cells or whole organisms as described herein, will lead to the production of a desired oligonucleotide such as an siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism.

Aptamers

Aptamer molecules specific for TLR2 protein can also be used. Aptamers are nucleic acid molecules having a tertiary structure that permits them to specifically bind to protein ligands (e.g., Osborne, et al., Curr. Opin. Chem. Biol., 1: 5-9 (1997); and Patel, Curr. Opin. Chem. Biol., 1: 32-46 (1997)). Since nucleic acid molecules may, in many cases, be more conveniently introduced into target cells than therapeutic protein molecules, aptamers offer a method by which TLR2 activity can be specifically decreased without the introduction of drugs or other molecules which may have pluripotent effects.

Determination of HSV Infection

As described herein, it is the host response (i.e., induction of TLR2 signaling) that causes the deleterious TLR2-mediated effects of HSV infection such as those observed in HSV infected neonates. Certain methods described herein relate to identification of compounds that inhibit TLR2 signaling in an HSV infected cell. In some embodiments such compounds would not be expected to significantly affect the infectivity of HSV into a cell treated with the compound, and thus can be useful for treating HSV infection. Accordingly, compounds that inhibit TLR2 signaling in an HSV infected cell can also be tested for their effect on infectivity. In general, the number of plaque forming units (pfu) in a tissue or cell that is contacted with a test compound that can decrease TLR2 signaling is determined and compared to the number of pfu in an infected cell that was not contacted with the compound. Infectivity can be measured as described herein or using other methods known in the art. A compound that affects TLR2 signaling, but does not affect the amount of virus, is thus a TLR2-targeted compound that can bes useful for treating HSV infection. A compound that is acceptable for such a use may or may not decrease infectivity.

Compounds that are identified as useful for treating HSV infection can also be tested, e.g., using methods described herein, for their ability to inhibit TLR2 signaling that is associated with HSV infection. Thus, the methods include the identification of compounds that are particularly useful for treating HSV infection, e.g., in neonates.

Symptoms of HSV and TORCH Infection

In some methods, a compound is tested for its ability to ameliorate one or more symptoms of HSV infection. Symptoms of HSV infection in neonates, children, and adults are described herein and known in the art, e.g., *The Merck Manual, Seventeenth Edition*, Rahway, N.J., 1999-2004.

Common oral and genital HSV infections typically produce an eruption of tiny blisters on the skin or mucous membranes. Oral infection with HSV usually causes herpetic gingivostomatitis (mouth sores). In addition, affected persons generally feel sick and have a fever, headache, and body aches. The mouth sores can last 10 to 14 days and are often very severe, making eating and drinking extremely uncomfortable. In some first oral infections, swollen gums are the only symptom; occasionally, no symptoms develop. Herpetic gingivostomatitis most commonly develops in children. HSV-2 symptoms are usually mild and can include itching, burning, soreness and small blisters in the genital area; small skin ulcers, which form when the blisters break; localized pain, e.g., if urine touches the genital ulcers; enlarged and/or painful lymph nodes in the groin; and headache, fever and a general malaise.

The first genital HSV infection can be severe and prolonged, with multiple painful blisters in the genital region. Fever and general malaise are common, with burning during urination in some cases. Occasionally, the infected person may have no symptoms. Recurring attacks of genital herpes generally begin with typical symptoms (e.g., local tingling, discomfort, itching, or aching in the groin) that precede the blisters by several hours up to 2-3 days. Painful blisters, surrounded by a reddish rim, appear on the skin or mucous membranes of the genitals. The blisters quickly break open, leaving sores. In some cases, blisters also appear on the thighs, buttocks, or around the anus. Genital blisters may develop on the vulva in women; these blisters are usually obvious and very painful. Internal blisters may develop in the vagina or on the cervix; they are less painful and are not visible. Typical episodes of recurring genital herpes last about a week.

HSV-1 or HSV-2 occasionally will enter through a break in the skin, e.g., of a finger, causing a swollen, painful, red fingertip; this condition is known as herpetic whitlow.

HSV-1 sometimes infects the cornea of the eye, a condition known as herpes simplex keratitis, which features painful sores and blurred vision. Over time, the cornea can become cloudy, causing a significant loss of vision and requiring corneal transplantation.

TORCH Syndrome refers to infection of a developing fetus or newborn by any of a group of infectious agents, e.g., Toxoplasmosis, Other infections, Rubella, Cytomegalovirus, or Herpes. As used herein, "other infections" can include syphilis, hepatitis B, Coxsackie's virus, Epstein-Barr virus, varicella-zoster virus, and human parvovirus. Infection with any of these agents may cause a constellation of similar symptoms in affected neonates, including fever; difficulties feeding; small areas of bleeding under the skin, causing the appearance of small reddish or purplish spots; hepatosplenomegaly (enlargement of the liver and spleen); cutaneous manifestations, including petechiae, purpura, jaundice, and dermal erythropoiesis, hearing impairment; abnormalities of the eyes; and/or other symptoms and findings. Each infectious agent may also result in additional abnormalities that may be variable, depending upon a number of factors (e.g., stage of fetal development). In neonatal HSV infections, symptoms can include single or grouped cutaneous vesicles, oral ulcers, or conjunctivitis. See, e.g., Epps et al., Semin. Dermatol. 14 (2): 179-86 (1995).

Subjects most at risk of HSV infection include immunosuppressed individuals (e.g., individuals on an immunosuppressive regime or individuals infected with HIV).

Animal Models and Human Subjects

In some methods, it is desirable to confirm that a subject is infected with HSV. Such methods are known in the art (for example, *The Merck Manual, Seventeenth Edition*, Section. 19, Chapter 260; Merck & Co, Inc., Rahway, N.J., 1999-2004). For example, infection can be confirmed by infecting a cultured cell with a sample from a suspected infection site and isolating virus from the culture. Various cell lines of human or nonhuman origin can be used in this method. Retrieval of virus from a subject can be, e.g., from skin vesicles, the mouth, eye, or CSF (cerebrospinal fluid). In some neonates presenting with encephalitis, virus is found only in the brain. Testing can also be done using, e.g., polymerase chain reaction. Cytopathologic effects usually can be demonstrated in tissue culture within 24 to 48 hours after inoculation. The determination of HSV-1 infection can also be confirmed, for example, by neutralization with appropriate high-titer antiserum; immunofluorescence of lesion scrapings (e.g., using monoclonal antibodies that specifically bind to HSV-1); and electron microscopy. Such methods are useful in assays that relate to determining whether a compound (i.e., a compound that decreases TLR2 signaling) can decrease symptoms of HSV infection.

Animal models of HSV infection are known in the art, e.g., as described in Weber, Animal Models in Virology, in Schmidt and Weber (eds), *Animal Testing in Infectiology*. Contrib Microbiol. Basel, Karger, 2001, 9:15-30. For example, the murine model discussed herein can be used. Rodents, e.g., rats, mice, and guinea pigs, and lagomorphs, e.g., rabbits, also make good models of HSV infection, when exposed to an HSV.

Predictive Medicine

The methods described herein also pertain to the field of predictive medicine in which diagnostic assays, prognostic assays, and monitoring clinical trials are used for prognostic (predictive) purposes to thereby treat an individual infected with HSV. In particular, a patient infected with or exposed to HSV and at risk for a TLR2-mediated effect of HSV infection such as encephalitis, can be monitored for activation of TLR2 activity. Increased TLR2 activity in a subject infected with HSV indicates that the subject is at risk of developing a TLR2-mediated effect of HSV infection. Such subjects may then be monitored for early detection of adverse symptoms associated with TLR2 activity during HSV infection or administered prophylactic treatment to decrease TLR2 activity or treat symptoms associated with such infections.

Methods of determining TLR2 activity in a subject, e.g., in a sample from a subject, include assaying indicia of TLR2 activity, e.g., NF-κB activation, cytokine and/or chemokine production, e.g., IL-1, IL-6, tumor necrosis factor (TNF), MCP-1, MIP-1 α, and/or IL-8, e.g., by blood leukocytes or other tissues or serum cytokine/chemokine levels. Other indicia of TLR2 activity can also be assayed. Methods of assaying such indicia are known in the art.

Pharmaceutical Compositions

The compounds described herein that are useful for treating TLR2-mediated effects of HSV-1 infection can be incorporated into pharmaceutical compositions. Such compositions typically include the compound (e.g., nucleic acid molecule, peptide, or antibody) and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds such as antiviral drugs can also be incorporated into the compositions.

A pharmaceutical composition is formulated to be compatible with its intended route of administration. Examples of routes of administration include parenteral (e.g., intravenous, intradermal, subcutaneous, inhalation, transdermal (topical), transmucosal, and rectal) or oral administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens;

antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars or polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Lipofectin® or liposomes can be used to deliver a compound (e.g., a polypeptide or an antibody or a fragment of the Fab region that binds TLR2) into cells. Polypeptides, antibodies and fragments thereof, e.g., single chain neutralizing antibodies that bind to TLR2 can also be administered, for example, by expressing nucleotide sequences encoding the polypeptides within the target cell population (see, e.g., Marasco et al., Proc. Natl. Acad. Sci. USA, 90: 7889-7893 (1993)).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained from commercial sources such as Alza Corporation (Mountain View, Calif.). Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Described herein are agents (compounds) that modulate TLR2 expression or activity in a subject infected with HSV. An agent can be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

An antibody (or fragment thereof) that can be used in the methods described herein can be conjugated to a second antibody to form an antibody heteroconjugate as described by Segal in U.S. Pat. No. 4,676,980.

The nucleic acid molecules described herein (e.g., nucleic acid molecules encoding therapeutically useful nucleic acid molecules, e.g., oligonucleotides including an antisense nucleic acid or siRNA targeting TLR2, and nucleic acid molecules encoding TLR2 dominant negative polypeptides) can be inserted into vectors and used to produce the oligonucleotides or nucleic acid molecules or for use as gene therapy vectors. Gene therapy vectors can be delivered to a subject by, for example, intravenous injection, local administration (see U.S. Pat. No. 5,328,470) or by stereotactic injection (see e.g., Chen et al., Proc. Natl. Acad. Sci. USA, 91: 3054-3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Compounds as described herein can be used for the preparation of a medicament for use in any of the methods of treatment described herein.

Methods of Treatment

The new methods include both prophylactic and therapeutic methods of treating a subject at risk of (or susceptible to) HSV-1 infection or having a disorder associated with HSV-1 infection and effects of the disorder associated with TLR2 activity. As used herein, the term "treatment" refers to the application or administration of a therapeutic agent to a subject (e.g., a human patient), or application or administration of a therapeutic agent to an isolated tissue or cell line from a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes, and antisense oligonucleotides as described supra.

In one aspect, the invention provides a method for preventing in a subject, a disease or condition associated with an aberrant or unwanted TLR2 expression or activity that is associated with HSV infection, by administering to the subject an agent that modulates TLR2 expression or at least one TLR2 activity. Subjects at risk for indications that are caused or contributed to by unwanted TLR2 expression or activity can be identified by, for example, any or a combination of diagnostic or prognostic assays as described herein. Administration of a prophylactic agent can occur prior to the manifestation of symptoms characteristics of the TLR2 expression or activity, such that undesirable effects of TLR2 activity (e.g., caused by HSV infection) are prevented or, alternatively, delayed in their progression.

A compound, e.g., an agent that inhibits TLR2 activity, e.g., identified using a method described herein, that proves to exhibit TLR2 inhibitory activity, can be used in accordance with the invention to prevent and/or ameliorate TLR2-mediated symptoms associated with HSV infection. Such molecules can include, but are not limited to: nucleic acids, polypeptides, peptides, phosphopeptides, small organic or inorganic molecules, or antibodies (including, for example, polyclonal, monoclonal, humanized, anti-idiotypic, chimeric or single chain antibodies, and Fab, $F(ab')_2$ and Fab expression library fragments, scFV molecules, and epitope-binding fragments thereof). Antibodies can be generated that are both specific for TLR2 and that decrease TLR2 activity. Antibodies or antigen-binding fragments thereof that decrease TLR2 activity are useful for treatment of undesirable TLR2-mediated effects that are associated with HSV-1 infection.

Antisense and ribozyme molecules that inhibit expression of TLR2 can also be used in accordance with the methods described herein to reduce the level of TLR2 expression, thus effectively reducing the level of TLR2 activity. Triple helix molecules and aptamers can also be utilized in reducing the level of TLR2 activity. Antisense, ribozyme, aptamers, and triple helix molecules are discussed above.

Compounds that inhibit TLR2 expression or activity can be administered to a patient at therapeutically effective doses to prevent, treat, or ameliorate HSV infection, e.g., in a neonate. A therapeutically effective dose refers to an amount of the compound sufficient to treat HSV infection as described herein. Toxicity and therapeutic efficacy of such compounds can be determined by standard pharmaceutical procedures as described herein.

Data obtained from cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models (e.g., in mouse or a primate) to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In some embodiments, a therapeutically effective amount of a therapeutic compound (e.g., a polypeptide (i.e., an effective dosage) ranges from about 0.001 to 30 mg/kg body weight/day, about 0.01 to 25 mg/kg body weight/per day, about 0.1 to 20 mg/kg body weight/day, about 1 to 10 mg/kg body weight/day, 2 to 9 mg/kg body weight/day, 3 to 8 mg/kg body weight/day, 4 to 7 mg/kg body weight/day, or 5 to 6 mg/kg body weight/day. The compound can be administered once, twice, or three times per day; or can be provided as a continuous infusion. In some cases, the compound is administered one time per week for between about 1 to 10 weeks, generally between 2 to 8 weeks, between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or can include a series of treatments.

In some embodiments, e.g., for antibodies, the dosage can generally be about 0.1 mg/kg of body weight/day (generally 10 mg/kg to 20 mg/kg). If the antibody is to act in the brain, a dosage of 50 mg/kg/day to 100 mg/kg/day may be appropriate. Generally, partially human antibodies and fully human antibodies have a longer half-life within the human body than other antibodies. Accordingly, lower dosages and less frequent administration are often possible with such compounds. Modifications such as lipidation can be used to stabilize antibodies and to enhance uptake and tissue penetration (e.g., into the brain). A method for lipidation of antibodies is described in Cruikshank et al. (J. Acquir. Immune. Defic. Syndr. Hum. Retrovirol., 14 (3): 193-203 (1997)).

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound that can modulate TLR2 activity (e.g., in an HSV infected cell) is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions (e.g., Ansell et al., Curr. Op. Biotechnol., 7: 89-94 (1996); Shea, Trends Polymer Sci., 2: 166-173 (1994)). Such "imprinted" affinity matrixes are amenable to ligand-binding assays, whereby the immobilized monoclonal antibody component is replaced by an appropriately imprinted matrix. An example of the use of such matrixes in this manner is described in Vlatakis et al. (Nature, 361: 645-647 (1993)). Through the use of isotope labeling, the "free" concentration of compound that modulates the expression or activity of TLR2 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiber optic devices, in turn allowing the dose in a test subject to be quickly optimized based on its individual $IC_{50}$. An rudimentary example of such a "biosensor" is discussed in Kriz et al. (Anal. Chem., 67: 2142-2144 (1995)).

Appropriate doses of a compound generally depend upon the potency of the compound with respect to the expression or activity to be modulated. When one or more of these compounds is to be administered to an animal or a human to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for a particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, it is generally desirable, although not required, to design a delivery system that targets such compounds to the site of affected tissue in to minimize potential damage to uninfected cells and, thereby, reduce side effects. For example, direct delivery of an inhibitor of TLR2 expression or activity to the CNS (e.g., by infusion into the CSF) is a method of delivery that can be used.

Another aspect of the invention pertains to methods of modulating TLR2 expression or activity for therapeutic purposes, e.g., treating HSV-1 infection. Accordingly, in an exemplary embodiment, the modulatory method of the invention involves contacting a cell (e.g., an HSV infected cell) with a compound that that decreases one or more of the activities of TLR2. A compound that decreases TLR2 activity can be a compound as described herein, such as a nucleic acid or a polypeptide. For example, the compound can be an antibody that specifically binds a TLR2 or a fragment thereof (a TLR2 antibody), a TLR2 antagonist, a peptidomimetic of a TLR2 antagonist, or other small molecule. Other examples of inhibitory agents include antisense nucleic acid molecules or siRNA molecules that are directed against TLR2. These modulatory methods can be performed in vitro (e.g., by culturing the cell with the agent) or, alternatively, in vivo (e.g., by administering the agent to a subject). As such, the present invention provides methods of treating an individual afflicted with an HSV infection that is characterized by aberrant or unwanted expression or activity of a TLR2 or nucleic acid molecule. For example, such activity is undesirable in a neonate. In one embodiment, the method involves administering an agent (e.g., an agent identified by a screening assay described herein), or combination of agents that modulates (e.g., down regulates) TLR2 expression or activity.

EXAMPLES

The invention is further illustrated by the following examples. The examples are provided for illustrative purposes only. They are not to be construed as limiting the scope or content of the invention in any way.

Example 1

HSV-1 Induces Cytokines Via TLR2

The ability of human cells, with or without TLRs on their surface, to respond to KOS strain herpes simplex virus-I was examined. An HEK293 cell line expressing human TLR2 was cloned as described in Kurt-Jones et al. (Blood, 100: 860-868 (2002)). HEK293 cell lines expressing human TLR3, TLR9, TLR4, and MD2 were described in Latz et al. (J. Biol. Chem., 277: 47834-47843 (2002)). The HEK293 cell lines were derived from the same parental HEK293 cells described in Lien et al. (J. Biol. Chem., 274: 33419-33425 (1999)).

To assay activation of TLR-mediated signaling, cells were transfected with an NF-κB firefly luciferase reporter plasmid and a control *Renilla luciferase* plasmid using GeneJuice™ transfection reagent. Transfected HEK293 cells were incubated overnight prior to challenge with virus or human IL-1β (100 ng/ml). Cells were then lysed and firefly luciferase activity was measured using Dual-Glo™ Luciferase Assay System (Promega, Madison, Wis.). Luciferase activity was calculated in RLU as a ratio of NF-κB-dependent firefly luciferase activity to NF-κB-independent *Renilla luciferase* activity.

HSV-1 KOS strain was used in the experiments described herein. Virus was grown in Vero cells (a cell line derived from African Green Monkey) and collected from cell supernatants as described in Brockman et al., J. Virol., 76: 3678-3687 (2002). In general, mice were infected by i.p. injection of $10^9$ (adult) or $10^4$ (neonate) pfu per mouse. Serum was collected in Gel Sep® tubes. Brains were homogenized in ice-cold sterile phosphate buffered saline containing 1% FCS (fetal calf serum) and 0.1% glucose. Virus titers were determined in plaque assays as described in Brockman et al., supra. For cytokine analysis, the homogenates were diluted 1:1 in PBS containing Complete™ protease inhibitors (Roche, Indianapolis, Ind.) and analyzed by ELISA. Homogenates were stored frozen at −70° C. prior to analysis.

The survival curves were compared using a generalized Wilcoxon test of Breslow as described in Stata Survival Analysis and Epidemiological Tables Reference Manual (Stata Statistical Software: Release 8.0, Stata Press, 2003 College Station Tex.). Cytokine levels were compared using the Kolmogorov Smirnov test as described in Stata Base Reference Manual (Stata Press, 2003).

Experiments with transfected human cells (HEK293) revealed that HSV-1 activates NF-κB through TLR2 (FIG. 1A) since stable TLR2 transfectants, but neither TLR3 nor TLR4 transfectants activated NF-κB in response to HSV-1 challenge. TLR9 transfectants were also unresponsive to HSV-1 (FIG. 1B) although recent reports suggests that HSV-1 and HSV-2 may signal through TLR9 Lund et al., J Exp Med, 198: 513-520 (2003); Krug et al., Blood (2003). These data demonstrate that TLR2 signaling is activated by HSV-1 infection.

To further define the role of TLRs as signal transducers for HSV-1, cytokine production by peritoneal exudate cells from wild type, TLR4 knockout, or TLR2 knockout mice was examined.

Mice deficient in TLR2, TLR4, or TLR6 were generated by gene targeting as described in Takeuchi et al., J. Immunol., 165: 5392-5396 (2000); Takeuchi et al., Int. Immunol., 13: 933-940 (2001); Takeuchi et al., J. Immunol., 169: 10-14 (2002); and Takeuchi et al., Immunity, 11: 443-451 (1999) and were provided as F2 interbred 129×C57BL/6 mice. Control mice were bred from C57BL/6×129 F2 mice obtained from Jackson Laboratories (B6129F2/J., Bar Harbor, Me.). All mice were bred and housed for at least three generations (and housed within the same room in the Animal Facility) prior to their inclusion in these experiments to minimize the effects of the environment on their susceptibility to infection.

Figure 1B:
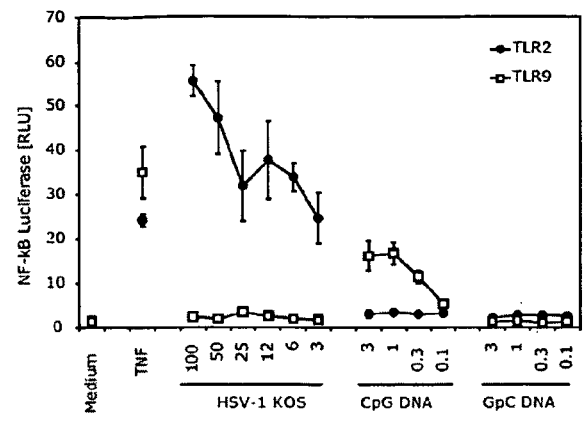
FIG. 1B is a graph illustrating the results of experiments in which HEK293 cells expressing human TLR2 or TLR9 were challenged with HSV-1 KOS (MOI 3-100), CpG DNA (0.1-3 μM), GpC control DNA (0.1-3 μM), or medium alone. NF-κB luciferase activity was measured as described above.
Figure 1C:
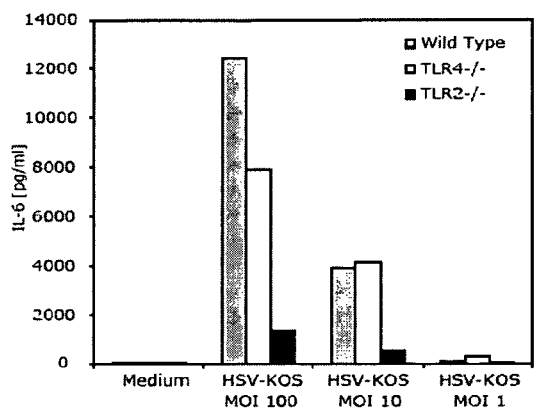
FIG. 1C is a bar graph depicting the results of experiments in which peritoneal exudate cells from wild type or TLR2$^{-/-}$ or TLR4$^{-/-}$ mice were stimulated with medium alone or with HSV-1 KOS at MOIs of 1, 10, and 100. IL-6 levels were measured in supernatants collected 16 hours after stimulation. The results are shown as the mean±SD of duplicate wells. Each mouse strain was tested in at least three independent experiments.

Wild type and TLR4$^{-/-}$ mouse peritoneal macrophages produced IL-6 in response to challenge with HSV-1. In contrast, peritoneal macrophages from TLR2$^{-/-}$ mice produced very little IL-6 in response to HSV-1 challenge (FIG. 1C). In control cultures, TLR2$^{-/-}$ macrophages also failed to respond to zymosan (TLR2 ligand) but did secrete IL-6 when challenged with LPS, a TLR4 ligand. These data confirm that TLR2 signaling is stimulated in response to HSV-1 infection. Thus, compounds that disrupt TLR2 signaling are useful for treating HSV-induced symptoms that are mediated by TLR2 signaling.

TLR2 is thought to signal as a heterodimer in combination with either TLR1 or TLR6. The response of TLR6 knockout, TLR2 knockout, and wild type peritoneal exudate cells to HSV-1 was compared.

To obtain cells from knockout and control mice, mice were injected with 4% thioglycollate and peritoneal exudate cells (PECs) were harvested 4 days later. PECs were plated at $10^6$ per well in 24-well plates and challenged with virus, phenol extracted LPS (lipopolysaccharide, 10 ng/ml, TLR4 ligand), zymosan (10 μg/ml, TLR2 ligand), IL-1□ (100 ng/ml) or medium alone. IL-6 and MCP-1 levels were determined by ELISA using BD Pharmingen OptEIA™ (San Diego, Calif.) and R&D DuoSet® (Minneapolis, Minn.) kits. All assays were done in duplicate.

Figure 1D:
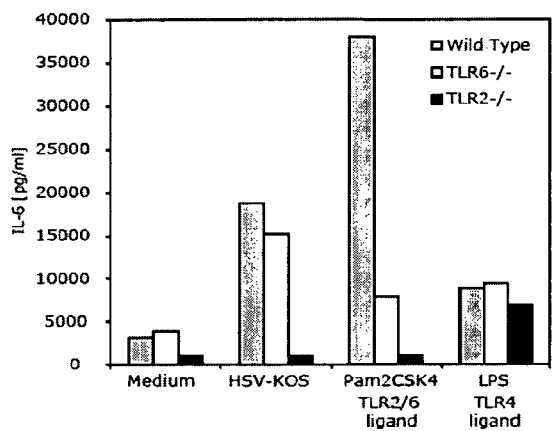
FIG. 1D is a bar graph illustrating the results of experiments in which wild type, TLR6$^{-/-}$, or TLR2$^{-/-}$ peritoneal exudate cells were challenged with HSV-1 KOS (MOI 100), Pam$_2$CSK$_4$ (100 ng/ml, a TLR2/TLR6 ligand), or LPS (10 ng/ml a TLR4 ligand). IL-6 levels were measured as described above.

Both wild type and TLR6−/− peritoneal macrophages secreted IL-6 when challenged with HSV-1 (FIG. 1D), indicating the TLR6 is not required for HSV-1 induced signaling. Thus, TLR1/TLR2 heterodimers are the mediators of TLR2 signaling associated with HSV-1 infection. Thus, compounds that disrupt the association between TLR1 and TLR2 are candidate compounds for treating HSV infection.

In addition to IL-6, challenge with HSV-1 induced MCP-1 secretion from peritoneal macrophages from wild type and TLR4$^{-/-}$, but not TLR2$^{-/-}$ mice. The induction of cytokines by HSV-1 was dose-dependent at multiplicites of infection up to 100 (FIGS. 1B and 1C). Both live and UV-irradiated HSV-1 induced IL-6 secretion from murine macrophages, indicating that viral replication was not required for cytokine induction.

Example 2

TLR2 Deficient Mice are Resistant to Lethal HSV-1 Challenge

Figure 2:
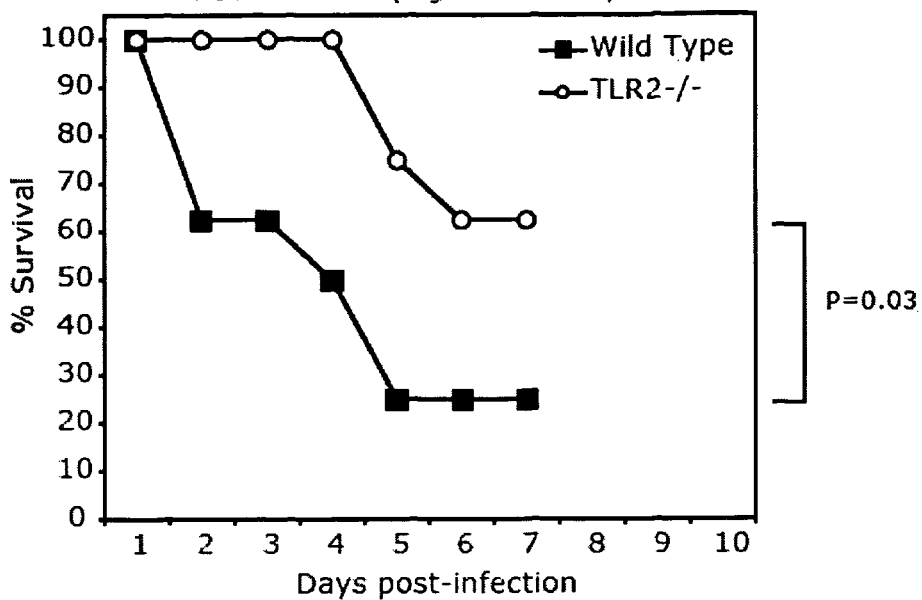
FIG. 2 is a line graph depicting the results of experiments in which groups of adult wild type (filled squares) or TLR2$^{-/-}$ (open circles) mice were challenged with $10^9$ pfu of HSV-1 KOS virus that was delivered i.p. Mice were observed for one week following challenge. Symptoms of HSV-1 infection seen in mice included lethargy, ruffled fur, hindlimb paralysis, and seizures. All surviving mice were free of symptoms. Each group included 8 mice, P≤0.03 for wild type versus TLR2$^{-/-}$ mice at day four.

The role of TLR2 in vivo during HSV infection was examined using a murine model of lethal HSV-1 encephalitis. Mice were infected with HSV-1 KOS strain that was delivered i.p. The mice were then monitored for encephalitis or death. Moribund animals exhibiting total paralysis and/or seizures were sacrificed. While wild type animals rapidly succumbed to infection, TLR2$^{-/-}$ mice had delayed death and an overall reduction in mortality. Five of eight TLR2$^{-/-}$ mice survived a challenge with 1-2×$10^9$ pfu of KOS virus, but only 2 of 8 wild type mice survived (FIG. 2, P=0.03 Wilcoxon test). Symptoms were also reduced in TLR2$^{-/-}$ mice compared to wild type or TLR4$^{-/-}$ mice. In a separate study (in which mice were sacrificed at day 4 for brain cytokine levels), 6 of 8 wild type and 6 of 8 TLR4$^{-/-}$ mice showed partial or total paralysis and/or seizures, while only 3 of 8 TLR2$^{-/-}$ mice were symptomatic. The symptoms in the TLR2$^{-/-}$ mice were milder than the wild type and TLR4$^{-/-}$ mice. For example, none of the TLR2$^{-/-}$ mice had either total paralysis or seizures.

These data show that TLR2 signaling is involved in the severe symptoms of HSV infection that are observed in infected animals. Furthermore, they demonstrate that elimination of TLR2 signaling causes significant improvement in the ability of an animal to survive infection and decreases the severity of symptoms.

Example 3

Neonatal HSV-1 Mortality is Greater in Wild Type than in TLR2$^{-/-}$ Mice

Figure 3:
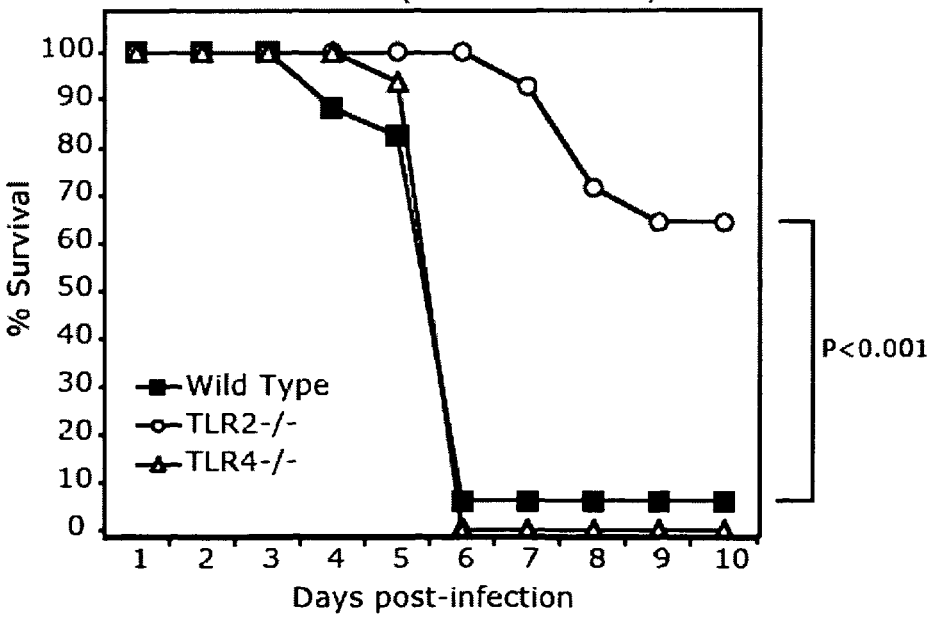
FIG. 3 is a line graph depicting the results of experiments in which groups of four-day-old wild type (filled squares), TLR4-/- (open triangles) or TLR2-/- (open circles) mice were challenged with $10^4$ pfu of HSV-1 KOS virus that was delivered i.p. Mice were observed for three weeks following the challenge. The symptoms of HSV-1 infection that were observed in neonatal mice included spasmodic limb movement, hindlimb and total paralysis, and bloating. There were 14-17 mice per group, P<0.001 for wild type versus TLR2$^{-/-}$ mice at day six.
Figure 4:
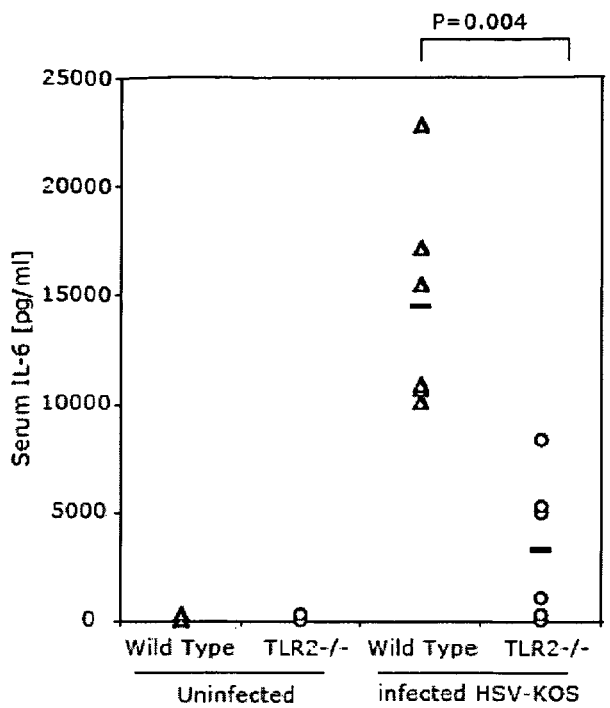
FIG. 4 is a graph depicting the results of experiments in which wild type (open triangles) or TLR2-/- (open circles) mice were infected with $10^9$ HSV-KOS i.p. or were not infected. Blood was collected 24 hours after infection and serum IL-6 levels were determined by ELISA. (P=0.004 for wild type versus TLR2$^{-/-}$ at 24 hours.)
Figure 5A:
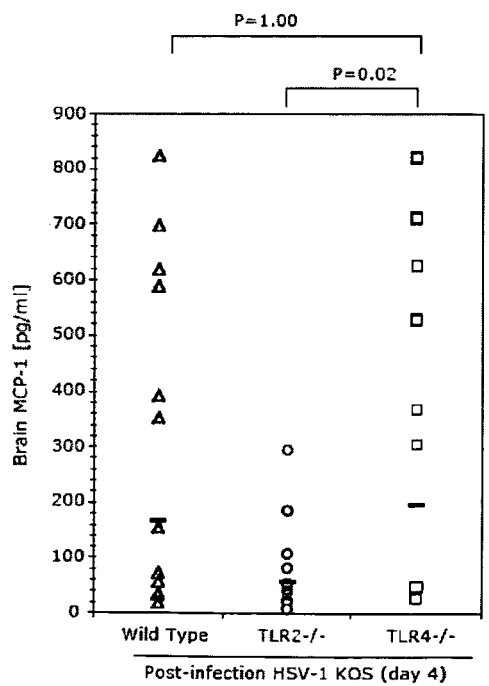
FIG. 5A is a graph depicting the results of experiments in which levels of MCP-1 in the brains of HSV-1 KOS infected wild-type (open triangles), TLR2-/- (open circles), and TLR4-/- (open squares) mice were determined using ELISA. MCP-1 levels in individual brains are shown. Geometric mean levels of MCP-1 are indicated by the bar.
Figure 5B:
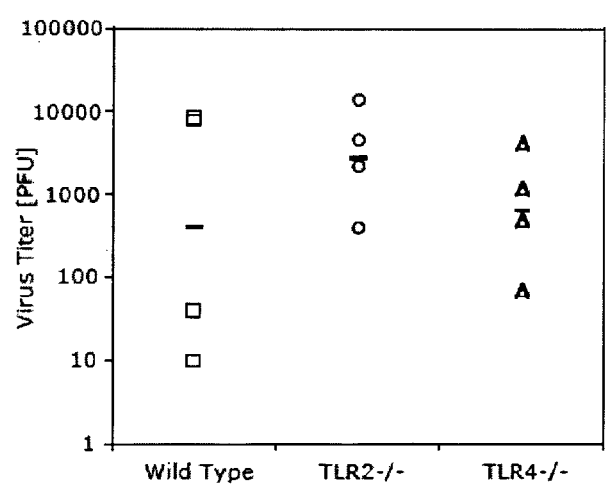
FIG. 5B is a graph depicting the results of experiments in which virus titers were determined in the brains of infected wild-type (open squares), TLR2-/- (open circles), and TLR4-/- (open triangles) mice. The results are expressed as the number of plaque forming units (pfu) of HSV-1 KOS in the brains of infected mice on day 4 post-challenge with virus that was delivered i.p. The levels of virus in individual brains are shown. Geometric mean pfu is indicated by the bar.
Figure 6A:
FIGS. 6A-I are a series of histopathology brain sections from HSV-1 KOS infected mice. The sections are reproductions of micrographs of hematoxylin/eosin stained sections from the cerebellums of wild type (6A, D and G), TLR4-/- (6B, E, and H) TLR2-/- (6C, F, and I) mice four days post-infection with HSV that was delivered i.p.
Figure 6B:
Figure 6C:
Figure 6D:
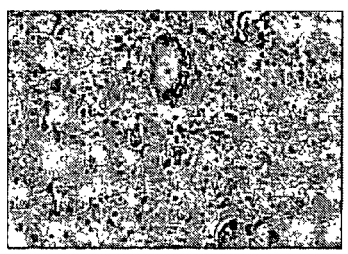
Figure 6E:
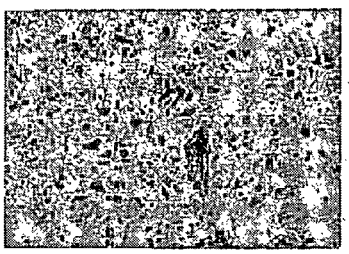
Figure 6F:
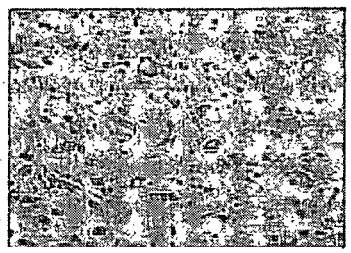
Figure 6G:
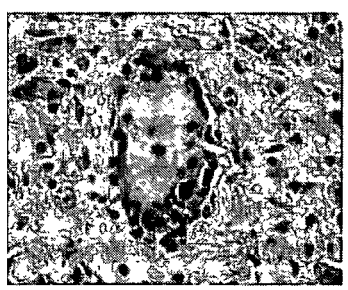
Figure 6H:
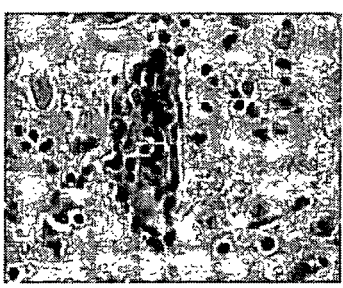
Figure 6I:
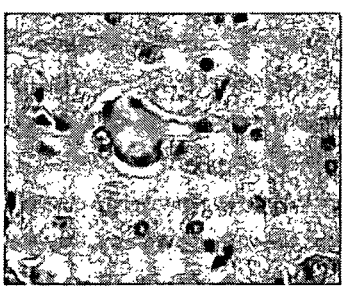

Adult mice, like adult humans, are less likely to succumb to HSV-1 challenge. On the other hand, neonates are highly susceptible to lethal HSV-1. Therefore, we examined the response to 4 day old mice to HSV-1 challenge. Neonates were injected with $10^4$ pfu HSV-1 i.p. and monitored for at least 14 days (FIG. 3). All neonates were well and developed normally for the first 4 to 5 days post-infection. Wild type and TLR4$^{-/-}$ neonates succumbed to HSV-1 challenge on day 6 post-infection (>90% lethality). In contrast, greater than 60% of the TLR2$^{-/-}$ neonates survived HSV-1 challenge. Remarkably, at least 50% of the TLR2$^{-/-}$ mice were symptom-free for the entire 2 week course of study and another 12% of the TLR2$^{-/-}$ neonates exhibited only mild, transient symptoms. TLR4$^{-/-}$ mice were indistinguishable from wild type mice, with rapid onset of paralysis and death on day 6 post-infection (FIG. 3).

The data demonstrate that TLR2 signaling mediates severe deleterious effects of HSV infection in neonates and that reduction of TLR2 signaling improves survival and decreases the severity of symptoms associated with HSV infection in neonates.

Example 4

Wild Type but Not TLR2 Knockout Mice have Elevated Serum IL-6 Levels After HSV-1 Challenge The effect of TLR2 deficiency on cytokine production in vivo was examined in HSV-1 infected animals. Wild type mice and TLR2$^{-/-}$ mice were challenged with HSV-1 ($2\times10^9$ pfu HSV-KOS i.p.). Elevated levels of IL-6 were found in the serum one day post-infection in wild type mice, whereas TLR2$^{-/-}$ mice had very little IL-6 in their serum (FIG. 4, $P<0.004$). Similarly, MCP-1 was detected in serum day 1 post-infection. Serum cytokine levels returned to baseline by day 2 post-infection.

These studies show that the acute production of inflammatory cytokines upon HSV-1 infection was dependent on TLR2 expression in the infected host.

Example 5

MCP-1 Levels are Elevated in the Brains of Wild Type but Not TLR-2 Knockout Mice In addition to cytokines, which are often essential to immune responses, interaction with TLRs also induces the production of chemokines such as MCP-1 from host cells. Accordingly, levels of MCP-1 were assayed in wild type, TLR2$^{-/-}$, and TLR4$^{-/-}$ mice that were infected with HSV-1 KOS that was delivered i.p. (109 pfu HSV i.p.). This dose was 50% lethal on day 4 in wild type, but not in TLR2$^{-/-}$ mice. Wild-type mice, but not TLR2$^{-/-}$ mice, were found to be moribund with brain hemorrhage at day 4. MCP-1 levels were measured in brain homogenates by ELISA. Wild type and TLR4$^{-/-}$ mice demonstrated high MCP-1 levels in their brains at day 1 after challenge. In all mice MCP-1 levels returned to baseline (<10 pg/ml) on days 2 and 3 post-challenge. When symptoms of encephalitis (e.g., animals were moribund, hemorrage, have seizures, paralysis, spasmodic limb movement, or bloating) appeared on day 4, a second wave of MCP-1 production in the brains was detected in wild type and TLR4 knockout mice (FIG. 5A). Brain MCP-1 levels in TLR4$^{-/-}$ mice were indistinguishable from levels in wild type mice ($P=1.00$). In contrast, significantly lower levels of MCP-1 were detected in the brains of TLR2$^{-/-}$ mice (FIG. 5A, $P=0.02$). At the same time as the increased MCP-1 production, significant hemorrhage was apparent in wild type brain tissue, while the TLR2$^{-/-}$ brains had a normal gross appearance.

Thus, compounds that inhibit the activation of TLR2 signaling in response to HSV-1 infection will decrease MCP-1 expression or activity compared to controls that are infected with HSV-1, but are not treated with the compound. Also, such compounds decrease hemorrage compared to controls and the gross brain morphology of an infected animal treated with the compound is improved (e.g., normal) compared to a control.

HSV-1 virus was detected in the brains of TLR2$^{-/-}$, as well as the wild type and TLR4$^{-/-}$ mice but levels of virus did not differ significantly between groups (FIG. 5B). These data demonstrate that while viral infectivity is not significantly affected by the lack of TLR2, the absence of TLR2 signaling can ameliorate the effects of viral infection.

These data also demonstrate that it is not necessary for a compound that is effective for treating TLR2-mediated symptoms of HSV-1 infection to reduce infectivity of the virus.

Example 6

Wild Type and TLR4 Knockout but Not TLR2 Knockout Mice have Inflammatory Lesions in the Brain After HSV-1 Challenge Microscopic examination of the of brains from HSV infected mice revealed mononuclear cell infiltrates and prominent perivascular cuffing in the medulla of wild type and TLR4 knockout mice. In contrast, TLR2 knockout animals had normal appearing brain tissue (FIGS. 6A-I). The lack of apparent pathology in the TLR2 knockout brains was particularly remarkable as virus titers in the brains of TLR2$^{-/-}$ mice did not differ from those in the brains of TLR4$^{-/-}$ and wild type mice (FIG. 5B). Thus, the host response rather than the virus itself is responsible for the pathologic changes in the brain in response to HIV infection.

Microscopic examination of brain pathology in HSV infected mice provides an additional assay for determining whether a compound that decreases TLR2 signaling is effective for decreasing deleterious effects of HSV infection in the brain.

Example 7

The Role of TLR2 in the Response to HSV-2

The experiments described above established a role for TLR2 in the response to HSV-1, but did not address the role of TLR2 in the response to HSV-2. While neonatal disease may involve destructive lesions of both the liver and the brain, many features suggest a “sepsis like” picture which could be related to the ability of these viruses to stimulate TLRs.

To examine the effect of HSV infection on the transcription of host proteins (particularly cytokines and chemokines), and to compare the response to HSV-1 and HSV-2, the ability of HSV-2 as well as HSV-1 to induce a cytokine (chemokine) response from human peripheral blood mononuclear cells was investigated (FIG. 7A). Challenge with either HSV-1 and HSV-2 activated cytokine (IL-6) and chemokine (IL-8) secretion from human peripheral blood mononuclear cells in a dose-dependent manner (FIG. 7A). HSV-1 and HSV-2 each induced NF-κB activation in TLR2-transfected HEK cells, but neither virus activated NF-κB in the TLR4-expressing or control HEK cells (FIG. 7B). In these experiments, virus was UV-inactivated prior to cell challenge, indicating that virus replication was not necessary for either activation of NF-κB or stimulation of cytokine secretion. As described herein, experiments performed with knock-out mice revealed an absolute requirement for TLR2 for cytokine production induced by HSV-1 and HSV-2.

Thus, normal adult leukocytes mount a robust innate immune response to both HSV-1 and HSV-2 challenge as measured by their production of inflammatory cytokines. The relative magnitude of in vitro responses observed with HSV-1 compared to HSV-2 may not correlate well with clinical outcomes because these studies use inactivated virus and do not account for any additional tissue destruction that may be caused by the viruses themselves. The high multiplicities of infection necessary to see these responses suggest that there is a threshold level of virus that is necessary to trigger the TLR response.

Example 8

Cytokine Responses in Neonatal and Adult Cells

There is evidence that neonates have exaggerated cytokine responses to certain microbial pathogens as compared to adults (Karlsson et al., Infect. Immun., 70: 6688-96 (2002)).

Figure 7A:
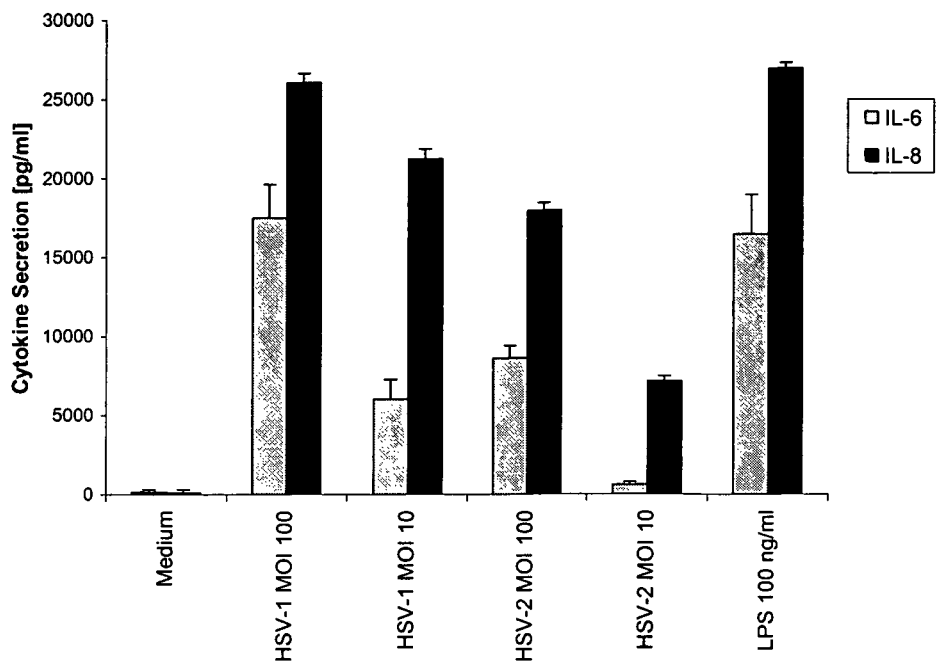
FIG. 7A is a bar graph showing human peripheral blood mononuclear cells stimulated with UV-inactivated HSV-1, UV-inactivated HSV-2 or LPS (positive control) for 18 hours. IL-8 and IL-6 levels in the culture supernatants were measured by ELISA. All experiments have been repeated multiple times with identical results. Error bars shown are based on triplicate wells.
Figure 7B:
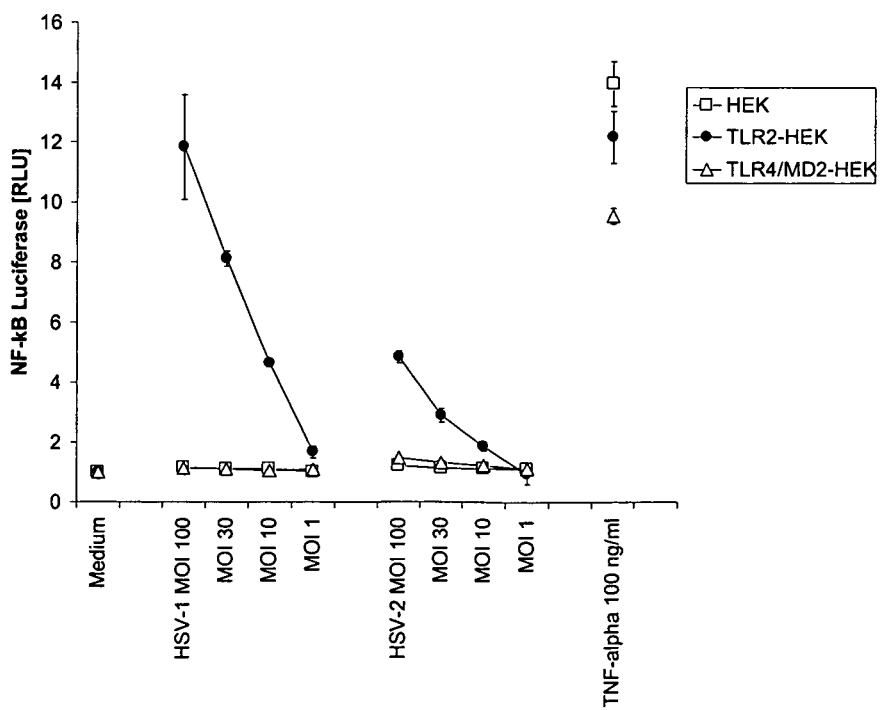
FIG. 7B is a line graph showing human embryonic kidney (HEK) 293 cells expressing human TLR2/CD14 or TLR4/MD2 and control HEK cells transfected with an NF-kappaB driven luciferase reporter gene and a control *Renilla luciferase* gene. The cells were stimulated with varying multiplicities of infection (MOI) of HSV-1 (KOS strain) and HSV-2 (186 strain) or with TNF-alpha (positive control) for 6 hours. Viruses were exposed to UV light prior to stimulating the cells to eliminate infectivity. The MOIs shown were based on titers prior to UV-inactivation. Luciferase activity was measured using DualGlo™ reagents and normalized using the *Renilla luciferase* activity.
Figure 8A:
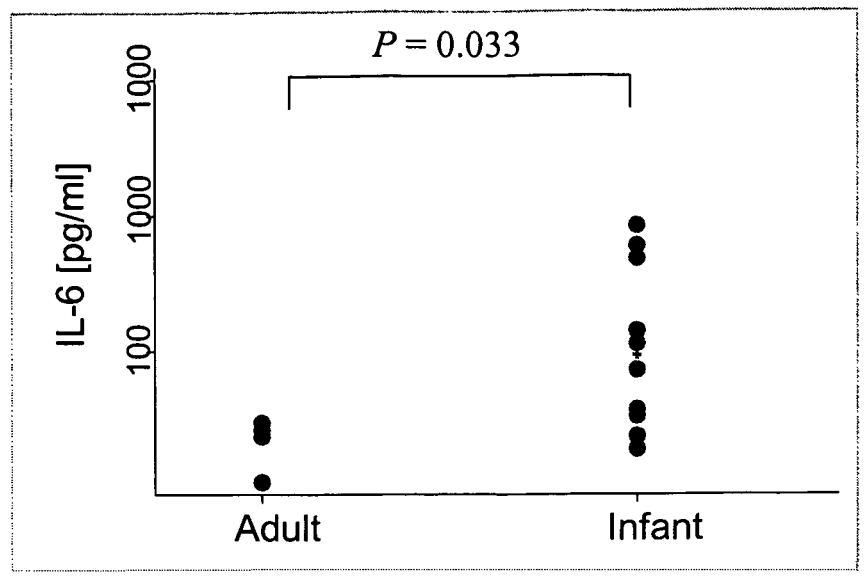
FIGS. 8A and 8B are dot plots showing the results of a comparison of adult and neonatal cytokine responses to HSV-1. Cord blood cells from 10 healthy newborns and peripheral blood from four healthy adults were stimulated with HSV-1 (MOI 40) for 18 hours. Medium alone (background) values were subtracted. P value is calculated using the rank-sum test (Mann-Whitney) to compare the groups. 8A: IL-6 levels (P=0.033) measure by ELISA. 8B: IL-8 levels (P=0.066) measured by ELISA.
Figure 8B:
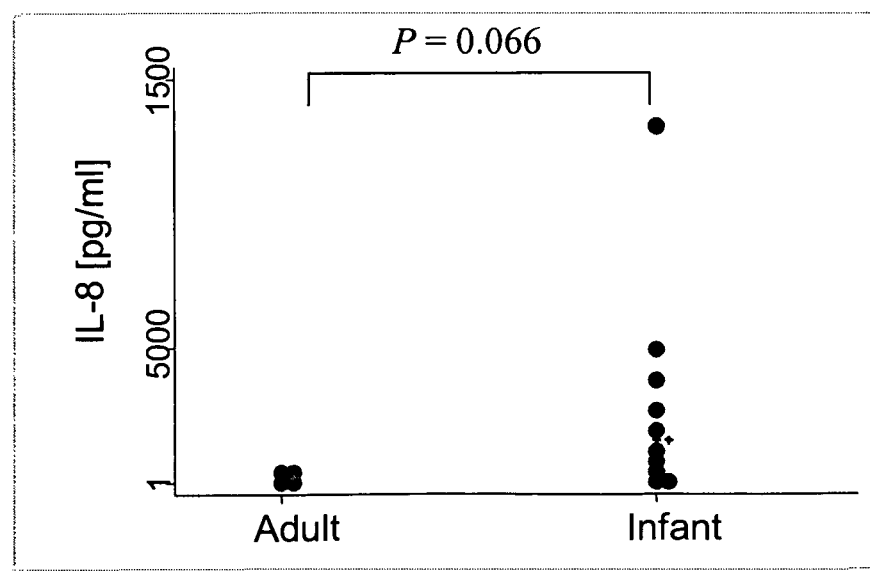

To determine whether these observations also applied to responses to HSV-1, the cytokine responses of neonatal and adult cells were compared. In this cohort of healthy neonates and adults, cytokine (IL-6 and IL-8) secretion in response to HSV-1 challenge was quantified using whole blood assays. In whole blood assays (FIGS. 8A-B), the levels of cytokine secretion are lower on a per cell basis than the levels in cultures of isolated mononuclear cells (FIGS. 7A-B). However, both polymorphonuclear and mononuclear cells are represented in whole blood. Moreover, whole blood cultures use autologous serum rather than exogenous fetal calf serum as the source of soluble accessory proteins such as CD 14. Therefore, whole blood assays are likely to more accurately reflect the functional capacity of the donor to respond to a microbial challenge. Based on a clinical case of a neonate with disseminated HSV-1 disease who had elevated levels of serum cytokines, the cytokine responses of adults and neonates to HSV-1 were examined. Analysis of the IL-6 response revealed that cord blood cells from neonates produce significantly higher levels of IL-6 in response to HSV stimulation than adult blood cells (FIG. 2A). Similarly, neonatal blood cells secreted higher levels of IL-8 than adult blood cells (FIG. 2B).

Thus, examination of the host responses of neonates to HSV indicates that rather than producing less IL-6 and IL-8 in response to HSV than adults, neonates produce more of these cytokines than adults.

Why is the disease seen in neonates so different from that seen in older children or adults? The host responses of neonates are deficient in many ways. Defects in both polymorphonuclear leukocyte production and migration as well as complement levels and interferon production have been documented (Kohl et al., J. Immunol., 136: 3038-44 (1986); Wilson, J. Pediatr., 108: 1-12 (1986)). In addition, macrophages of neonatal animals have less antiviral activity than macrophages from adult mice (Hirsch et al., J. Immunol., 104: 1160-5 (1970)). Thus, it would be expected that neonates would have higher levels of virus than adults. However, the symptoms of most infectious diseases (e.g., fever, vascular instability, or thrombocytopenia) are thought to be caused not by the bacterial or viral invaders themselves, but by the host response to antigens on these microbes.

The data described herein, documenting an exuberant neonate cytokine and chemokine response to HSV-1, provide a possible explanation for the unique clinical presentation of herpes group viruses in neonates compared to adults. Rather than being less responsive than adults, the neonatal response to certain antigens, particularly those in which the innate immune response is through TLR2, may be even stronger than those seen in adults (Karlsson et al., Infect. Immun., 70: 6688-96 (2002); Schultz et al., Pediatr. Res., 51:317-22 (2002)).

The clinical constellation of findings that typify disseminated neonatal herpes virus infections includes fever, tachycardia, hemodynamic instability, and laboratory abnormalities (including leukocytosis and thrombocytopenia). These clinical and laboratory findings are commonly associated with production of inflammatory cytokines. The discovery that Toxoplasmosis (Mun et al., Int. Immunol., 15: 1081-7 (2003)), Cytomegalovirus (Compton et al., J. Virol., 77: 4588-96 (2003)) and HSV (and, possibly, Rubella) are all TLR2 ligands suggest that the common clinical features of the TORCH diseases (McIntosh, Viral Infections of the Fetus and Newborn, in Avery and Taeusch, Eds., *Schaffer's Diseases of the Newborn*. 5$^{th}$ ed., Philadelphia, Pa., W. B. Saunders, 1984; Overall, Jr. and Glasgow, J. Pediatr., 77: 315-33 (1970)) may relate to the common interaction of these pathogens with TLR2. Thus, therapies that bind and block TLR proteins on the surface are likely to be useful in the treatment of these diseases.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing toll-like receptor 2 (TLR2) mediated inflammation associated with herpes simplex virus (HSV) infection in a subject in need thereof, the method comprising:
   identifying a subject with HSV who has or is at risk for developing TLR2 mediated inflammation associated with HSV; and
   administering to the subject a therapeutically effective amount of a TLR2 antisense nucleic acid or small interfering RNA (siRNA) for a period of time and under conditions sufficient to promote a decrease in the expression of TLR2 mRNA, wherein the antisense nucleic acid or siRNA specifically targets all or a portion of human TLR2 mRNA (SEQ ID NO:1) and promotes a decrease in the expression of TLR2 mRNA upon binding thereto, thereby reducing TLR2 mediated inflammation associated with HSV infection in the subject.

2. The method of claim 1, wherein the subject is a human.

3. The method of claim 1, wherein the subject is a child or an adult.

4. The method of claim 1, wherein the subject is a neonate.

5. The method of claim 1, wherein the subject has at least one symptom of encephalopathy.

6. The method of claim 5, wherein the method ameliorates a symptom of encephalopathy in the subject.

7. The method of claim 6, wherein the symptom of encephalopathy is selected from the group consisting of malaise, fever, headache, nausea, lethargy, confusion, delirium, seizures, aphasia, cranial nerve deficits, and hemiparesis.

8. The method of claim 5, wherein the subject is a neonate and the method ameliorates a symptom of Toxoplasmosis, Other Agents, Rubella, Cytomegalovirus, Herpes Simplex (TORCH) syndrome in the subject.

9. The method of claim 8, wherein the symptom is selected from the group consisting of fever, difficulties feeding, hepatosplenomegaly, cutaneous manifestations, hearing impairment, and abnormalities of the eyes.

10. The method of claim 9, wherein the cutaneous manifestations are selected from the group consisting of petechiae, purpura, jaundice, and dermal erythropoiesis.

11. The method of claim 5, wherein the method ameliorates a symptom selected from the group consisting of blisters on the cornea, skin or mucous membranes, itching, burning, soreness, skin ulcers, enlarged and/or painful lymph nodes in the groin, blurred vision, headache, fever, burning during urination, and general malaise in the subject.

12. The method of claim 1, wherein the HSV is HSV-1 or HSV-2.

13. The method of claim 1, wherein the antisense nucleic acid or siRNA is a double stranded siRNA that specifically targets human TLR2 mRNA (SEQ ID NO:1), wherein one of the strands comprises 16 to 30 contiguous nucleotides of SEQ ID NO:1, the other strand is complementary to the first strand, and the siRNA reduces human TLR2 mRNA expression in a cell.

14. The method of claim 13, wherein the antisense nucleic acid or siRNA is an antisense nucleic acid comprising at least 20 contiguous nucleotides of SEQ ID NO:1 or the complement thereof that reduces human TLR2 mRNA expression in a cell.

15. The method of claim 1, wherein the subject at risk for developing TLR2 mediated inflammation associated with HSV is infected with HSV and does not have TLR2 inflammation.

16. A method of reducing herpes simplex virus (HSV)-dependent expression of IL-6, NF-κB, or both IL-6 and NF-κB, in a human cell, the method comprising:
   obtaining a cell comprising HSV; and
   contacting the cell with a therapeutically effective amount of a TLR2 antisense nucleic acid or siRNA that specifically targets human TLR2 mRNA (SEQ ID NO:1) and thereby decreases human TLR2 mRNA expression, thereby reducing HSV-dependent expression of IL-6 or NF-κB, or both IL-6 and NF-κB in the cell.

* * * * *

UNITED STATES PATENT AND TRADEMARK OFFICE
CERTIFICATE OF CORRECTION

PATENT NO. : 8,748,403 B2  
APPLICATION NO. : 11/041065  
DATED : June 10, 2014  
INVENTOR(S) : Evelyn A. Kurt-Jones et al.

Page 1 of 1

It is certified that error appears in the above-identified patent and that said Letters Patent is hereby corrected as shown below:

On the title page, item (56) References Cited - OTHER PUBLICATIONS, column 2, line 15, delete "Deliverying" and insert -- Delivering --.

Signed and Sealed this
Twenty-sixth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,748,403 B2
APPLICATION NO. : 11/041065
DATED : June 10, 2014
INVENTOR(S) : Kurt-Jones et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1514 days.

Signed and Sealed this
Eighth Day of September, 2015

Michelle K. Lee
*Director of the United States Patent and Trademark Office*